(12) United States Patent

Jose et al.

(10) Patent No.: US 12,635,929 B2
(45) Date of Patent: May 26, 2026

(54) PACE PULSE DETECTION IN CARDIAC SIGNALS

(71) Applicant: Texas Instruments Incorporated, Dallas, TX (US)

(72) Inventors: Nithin Jose, Bangalore (IN); Anand Hariraj Udupa, Bangalore (IN); Sachin Aithal, Bangalore (IN); Raja Reddy Patukuri, Bengaluru (IN); Ashin Antony, Kochi (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 394 days.

(21) Appl. No.: 18/204,143

(22) Filed: May 31, 2023

(65) Prior Publication Data

US 2024/0057923 A1 Feb. 22, 2024

(30) Foreign Application Priority Data

Aug. 22, 2022 (IN) .............................. 202241047678

(51) Int. Cl.
*A61B 5/347* (2021.01)
*A61B 5/00* (2006.01)
*A61B 5/256* (2021.01)

(52) U.S. Cl.
CPC .............. *A61B 5/347* (2021.01); *A61B 5/256* (2021.01); *A61B 5/7203* (2013.01)

(58) Field of Classification Search
CPC ......... A61B 5/256; A61B 5/346; A61B 5/347; A61B 5/7203
See application file for complete search history.

(56) References Cited

U.S. PATENT DOCUMENTS

| | | | |
|---|---|---|---|
| 8,903,479 B2 | 12/2014 | Zoicas | |
| 9,462,956 B2 | 10/2016 | Pandia et al. | |
| 2008/0055150 A1* | 3/2008 | Hou ....................... | G01S 13/782 342/36 |
| 2015/0092765 A1 | 4/2015 | Ho | |
| 2016/0022164 A1* | 1/2016 | Brockway ............. | A61B 5/7203 600/509 |
| 2022/0001184 A1* | 1/2022 | Nallathambi ........ | A61B 5/1102 |

* cited by examiner

*Primary Examiner* — George Manuel

(74) *Attorney, Agent, or Firm* — Xianghui Huang; Frank D. Cimino

(57) ABSTRACT

Systems, apparatus, articles of manufacture, and methods are disclosed to detect a pace pulse in an electrocardiogram (ECG) signal. An example apparatus includes programmable circuitry configured to execute instructions to: identify a leading edge of a pulse in an input signal based on an amplitude change; identify a transition time of the leading edge of the pulse; validate the leading edge of the pulse based on the amplitude change and transition time; identify a trailing edge of the pulse; determine a width of the pulse between the leading edge and the trailing edge; and validate the pulse based on the width.

20 Claims, 20 Drawing Sheets

110

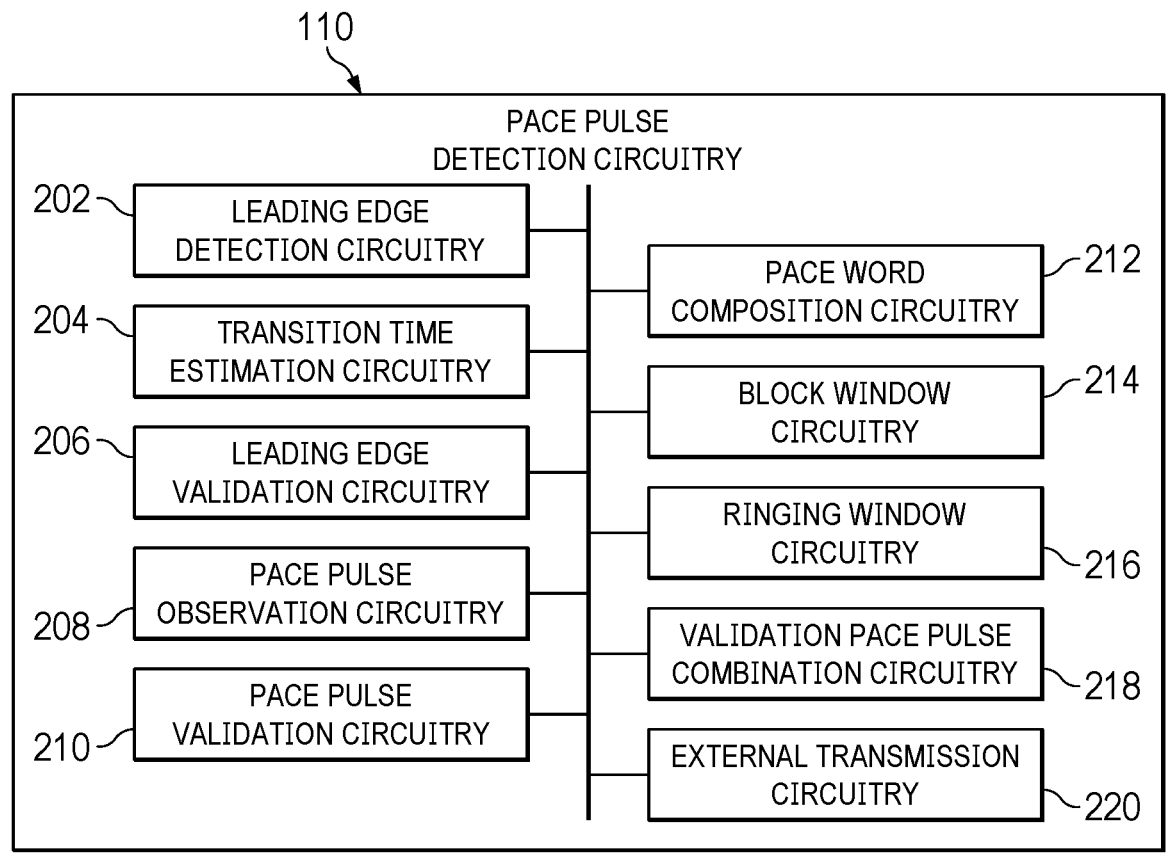

PACE PULSE
DETECTION CIRCUITRY

202 — LEADING EDGE DETECTION CIRCUITRY

204 — TRANSITION TIME ESTIMATION CIRCUITRY

206 — LEADING EDGE VALIDATION CIRCUITRY

208 — PACE PULSE OBSERVATION CIRCUITRY

210 — PACE PULSE VALIDATION CIRCUITRY

PACE WORD COMPOSITION CIRCUITRY — 212

BLOCK WINDOW CIRCUITRY — 214

RINGING WINDOW CIRCUITRY — 216

VALIDATION PACE PULSE COMBINATION CIRCUITRY — 218

EXTERNAL TRANSMISSION CIRCUITRY — 220

FIG. 2

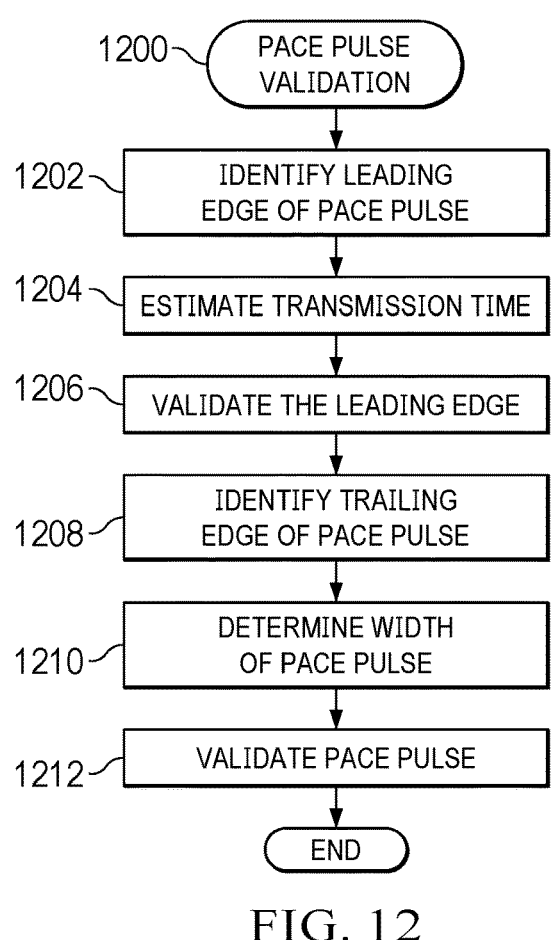

1200 — PACE PULSE VALIDATION

1202 — IDENTIFY LEADING EDGE OF PACE PULSE

1204 — ESTIMATE TRANSMISSION TIME

1206 — VALIDATE THE LEADING EDGE

1208 — IDENTIFY TRAILING EDGE OF PACE PULSE

1210 — DETERMINE WIDTH OF PACE PULSE

1212 — VALIDATE PACE PULSE

END

FIG. 12

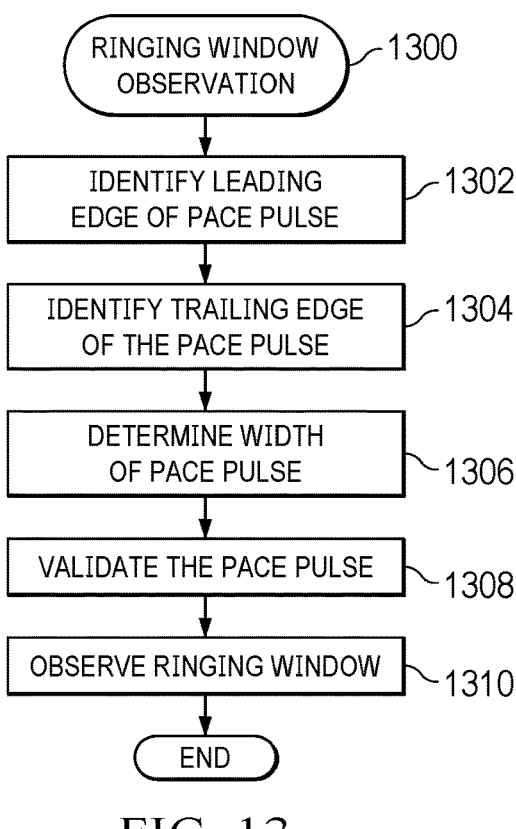

RINGING WINDOW OBSERVATION — 1300

IDENTIFY LEADING EDGE OF PACE PULSE — 1302

IDENTIFY TRAILING EDGE OF THE PACE PULSE — 1304

DETERMINE WIDTH OF PACE PULSE — 1306

VALIDATE THE PACE PULSE — 1308

OBSERVE RINGING WINDOW — 1310

END

FIG. 13

1400 — PACE PULSE DETECTION

1402 — GATHER ECG SIGNAL

1404 — FILTER SIGNAL

1406 — DETECT LEADING EDGE OF A PACE PULSE

1416 — ESTIMATE TRANSITION TIME

1422 — VALIDATE THE LEADING EDGE

1440 — OBSERVE PACE PULSE WINDOW

1452 — VALIDATE PACE PULSE

1466 — COMPOSE PACE WORD

1468 — OBSERVE BLOCK WINDOW

1470 — ADJUST METRIC THRESHOLDS

1472 — OBSERVE RINGING WINDOW

1474 — EXTERNALLY TRANSMIT DATA

END

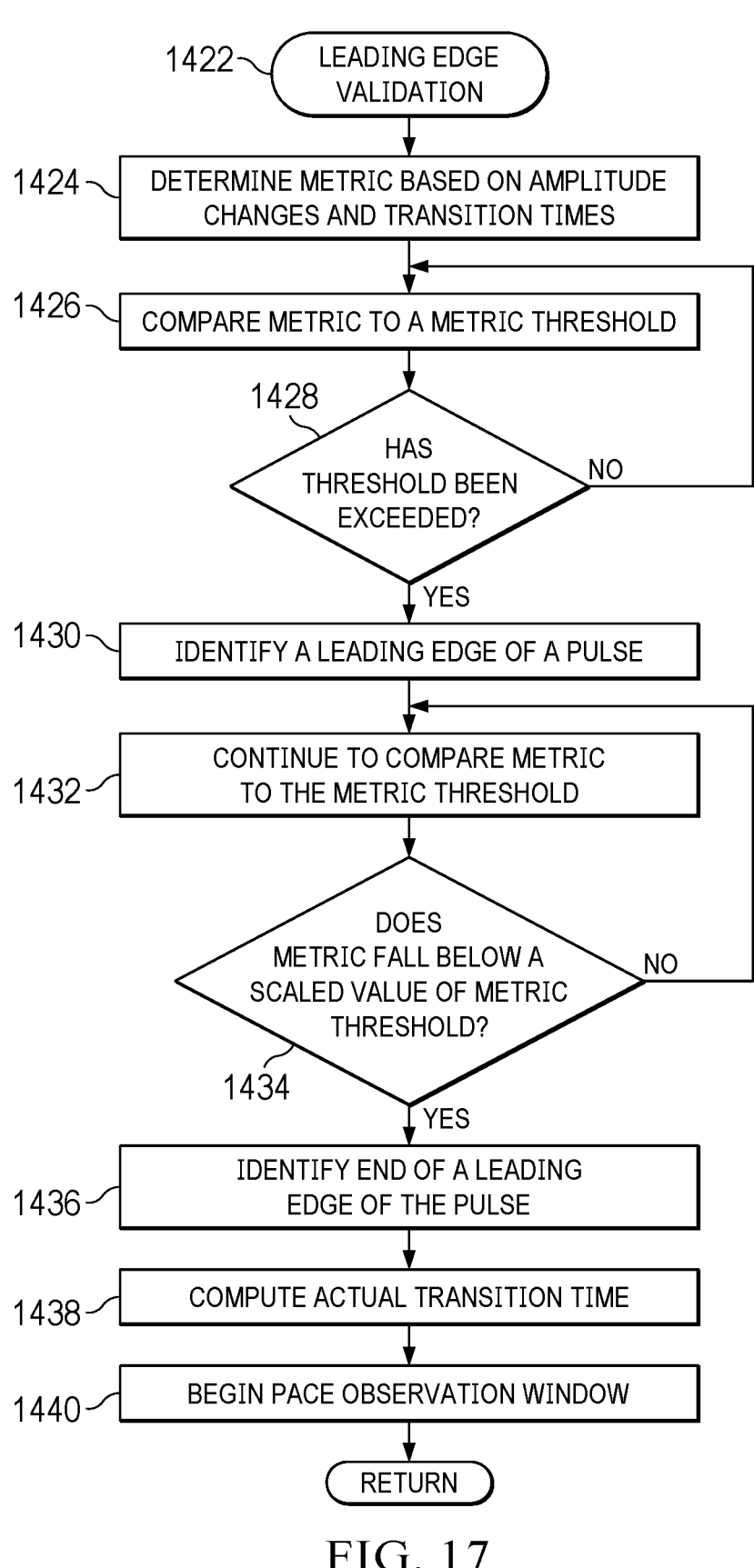

1422 — LEADING EDGE VALIDATION

1424 — DETERMINE METRIC BASED ON AMPLITUDE CHANGES AND TRANSITION TIMES

1426 — COMPARE METRIC TO A METRIC THRESHOLD

1428 — HAS THRESHOLD BEEN EXCEEDED?   NO

YES

1430 — IDENTIFY A LEADING EDGE OF A PULSE

1432 — CONTINUE TO COMPARE METRIC TO THE METRIC THRESHOLD

DOES METRIC FALL BELOW A SCALED VALUE OF METRIC THRESHOLD?   NO

1434

YES

1436 — IDENTIFY END OF A LEADING EDGE OF THE PULSE

1438 — COMPUTE ACTUAL TRANSITION TIME

1440 — BEGIN PACE OBSERVATION WINDOW

RETURN

FIG. 17

PACE PULSE DETECTION IN CARDIAC SIGNALS

CROSS-REFERENCE TO RELATED APPLICATION

This patent application claims the benefit of and priority to Indian Patent Provisional Application No. 202241047678, which was filed on Aug. 22, 2022, and is hereby incorporated herein by reference in its entirety.

TECHNICAL FIELD

This disclosure relates generally to patient monitoring and, more particularly, to pace pulse detection in cardiac signals.

BACKGROUND

Patient cardiac activity can be measured through electrodes that gather data of electrical activity that is represented in an electrocardiogram (ECG). Some patient monitoring systems analyze cardiac data to detect if a patent has an implanted pacemaker.

SUMMARY

Systems, apparatus, articles of manufacture, and methods are disclosed to detect a pace pulse in an electrocardiogram (ECG) signal. An example apparatus includes programmable circuitry configured to execute instructions to: identify a leading edge of a pulse in an input signal responsive to an amplitude change; identify a transition time of the leading edge of the pulse; validate the leading edge of the pulse based on the amplitude change and transition time; identify a trailing edge of the pulse; determine a width of the pulse between the leading edge and the trailing edge; and validate the pulse based on the width.

An example method includes identifying a leading edge of a pulse in a cardiac signal responsive to an amplitude change; identifying a trailing edge of the pulse; determining a width of the pulse between the leading edge and the trailing edge; validating the pulse based on the width; and observing a ringing window after a validation of the pulse, during the ringing window a threshold for identifying the leading edge is scaled.

An example non-transitory machine readable storage medium includes instructions to cause programmable circuitry to: identify a leading edge of a pulse in an input signal responsive to an amplitude change; identify a transition time of the leading edge of the pulse; validate the leading edge of the pulse based on the amplitude change and transition time; identify a trailing edge of the pulse; determine a width of the pulse between the leading edge and the trailing edge; validate the pulse based on the width; and observe a ringing window after validating the pulse, during the ringing window a threshold for identifying the leading edge is scaled.

BRIEF DESCRIPTION OF THE DRAWINGS

FIG. 2 is a block diagram of an example implementation of the pace pulse detection circuitry of FIG. 1.

FIGS. 12-19 are flowcharts representative of example machine readable instructions and/or example operations that may be executed, instantiated, and/or performed by example programmable circuitry to implement the pace pulse detection circuitry of FIG. 2.

In general, the same reference numbers will be used throughout the drawing(s) and accompanying written description to refer to the same or like parts. The figures are not necessarily to scale.

DETAILED DESCRIPTION

Figure 1:
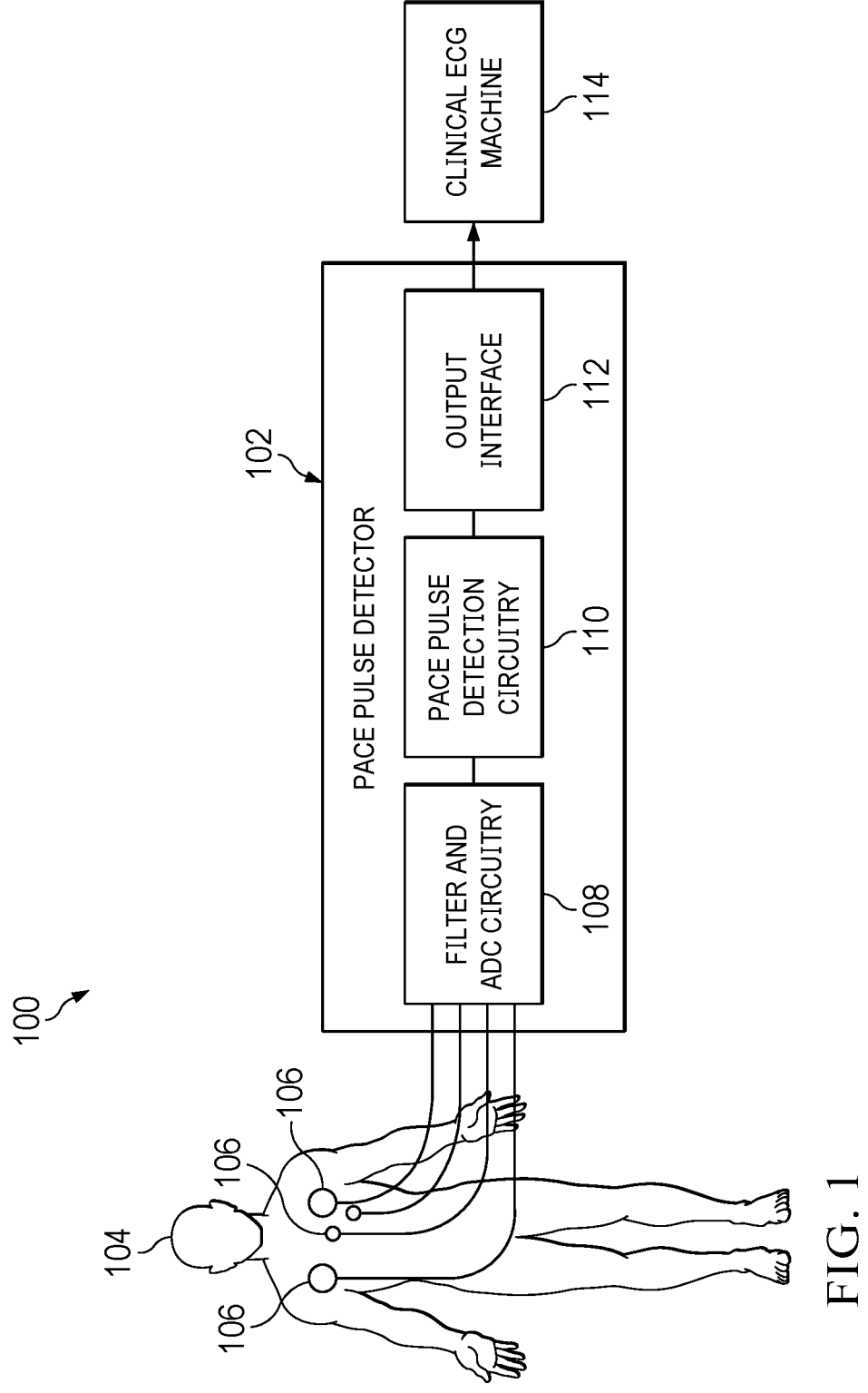
FIG. 1 is a block diagram of an example environment that includes an example pace pulse detector.

Pacemakers are electrical devices that create artificial cardiac pulses that are applied to one or more chambers of a patient's heart. Artificial cardiac pulses may be described as "pace pulses," "pace events," "pace pulse events," or simply "pulses" throughout this disclosure. The pulses cause the chamber of the heart to contract to pump blood and regulate the patient's heart rate. Pacemakers are used to treat, for example, arrhythmias, slow heart rate, enlarged or thickened heart muscles, and heart failure. There are different types of pacemakers including, for example, single chamber pacemakers with one electrical lead attached to the upper heart chamber or the lower heart chamber. Dual-chamber pacemakers have two electrical leads, one for the upper heart chamber and the other for the lower heart chamber. Biventricular pacemakers have three electrical leads used to coordinate contractions of the left and right ventricles. Pacemakers are implanted and, therefore, not visible to medical professionals. It is important for medical professionals who are monitoring or treating a patient to know if a patient has a pacemaker and/or to determine if a pacemaker is functioning properly.

Pacemakers emit periodic pulses that can be detected using the same electrodes as the ones used for electrocardiogram (ECG) measurement. The pace pulse appears as a short pulse superimposed on the ECG waveform. Some clinical ECG systems analyze all of the data in an ECG waveform to identify a pace pulse. Such solutions involve a continuous readout and analysis of high-speed data and transfer of data from an ECG analog front end (AFE) and a microcontroller unit (MCU), resulting in increased processing power and cost. Power consumption is a concern for battery-operated clinical ECG systems.

Examples described herein include an ECG AFE that has an internal pace detection engine or pace pulse detector that detects pace pulses. The detection of pace pulses in the ECG AFE reduces the burden on the signal chain further down (e.g., to a clinical ECG machine). In other words, less data is transferred from the ECG AFE for analysis and detection of a pace pulse.

Examples described herein also avoid false detection of pace pulses. Glitches in data not related to pace pulses can trigger false detections and can cause real events (i.e., real pace pulses) to be missed. Described examples validate a leading edge of the pace pulse to avoid analysis of glitches and/or missed pace pulses.

Pace pulses usually have a relationship between width (i.e., duration) and amplitude. In some examples, long pace pulses have lower amplitude, and short pace pulses have higher amplitudes. This relationship is based on the pacemaker delivering an amount of energy to activate the heartbeat. In some examples, the relationship between amplitude and width is an inverse relationship. Examples described herein measure the amplitude and width of the pace pulse and compare these parameters against a reference mask or model to validate the pace pulse.

In some examples, the signal chain for pace pulse detection includes notch filters that eliminate certain tones that are in the signal band of the pace pulse. For example, the signal band may include tones due to the excitations used for AC lead detection (e.g., 2 kHz) and/or a respiration impedance or excitation measurement (e.g., 64 kHz). These filters can cause long ringing artifacts after of a pace pulse. The ringing could cause the pace pulse detection to become corrupted during the time such ringing persists. In some examples described herein, a blocking window is observed after a pace pulse is detected. Further analysis efforts to detect a pace pulse are prevented in the blocking window. The duration of the blocking window may be based on, for example, a type of pace pulse to be detected. For example, biventricular pace pulses can have two pulses in succession. Accordingly, the blocking window is set to a duration short enough to detect the second pulse. Examples described herein detect pace pulses, account for ringing artifacts, and enable detection of a closely spaced second pace pulse.

FIG. 1 is a block diagram of an example environment 100 in which an example pace pulse detector 102 operates to detect if a patient 104 has a pacemaker. The environment 100 includes the pace pulse detector 102 coupled to a clinical ECG machine, and the environment 100 also includes electrodes 106 attached to a patient 104.

The ECG electrodes 106 provide electrical data from the patient 104 to the pace pulse detector 102 for analysis. In some examples, the pace pulse detector 102 is included in an AFE of a clinical ECG system (e.g., the clinical ECG machine 114). In other examples, the pace pulse detector 102 is included in an AFE of a separate device coupled between the electrodes and the clinical ECG machine 114. In some examples, the pace pulse detector 102 is an application-specific integrated circuit (ASIC). In some examples, the pace pulse detector 102 implements multichannel, simultaneous sampling, 24-bit, delta-sigma (ΔΣ) analog-to-digital converters (ADCs) using built-in programmable gain instrumentation amplifiers (INAs), an internal reference, and an on-chip phase-locked loop (PLL). In some examples, the pace pulse detector 102 incorporates features that are used in ECG and electroencephalogram (EEG) applications. In some examples the pace pulse detector 102 includes an internal receiver (e.g., including analog processing circuitry, an ADC, and digital processing circuitry), a switch matrix, and a control engine to detect a pace pulse present in an input signal, e.g., a cardiac signal collectively provided by the electrodes 106. The input signal is also referred to as an ECG signal, in this example, since at least some portions of the input signal will be provided to the clinical ECG machine 114 for further processing and/or display.

In the example of FIG. 1, the pace pulse detector 102 includes example filter and ADC circuitry 108, example pace pulse detection circuitry 110, and an example output interface 112.

One or more filters of the filter and ADC circuitry 108 condition the analog ECG signal from the electrodes 106. Filtering may be carried out both pre- and post-ADC conversion. For example, the filters remove background noise and other tones in the ECG signal including, for example, tones due to AC lead biasing and patient respiration. A combination of filters may be utilized for noise removal. For example, decimation filters may be used at the output of the ADC to remove noise that is common to ECG and pace signal paths. In one example, the filters may be implemented using a combination of a decimation by 4 cascaded integrator-comb (CIC) 3 filter, a decimation by 2 cic4 filter, and a decimation by 2 cic4 filter. After passing through this example set of filters the ECG signal from the ADC output will be decimated by 16. Filter combinations such as these may also be used for ECG and pace data paths.

A programmable or fixed lowpass filter(s) may be used to remove, for example, the 10 kHz to 20 kHz frequencies that may be present in the pace path. Pace path filtering may be implemented using a finite impulse response (FIR) filter with programmable cutoff frequency of either 10 kHz or 20 kHz. In one example, the filter may be an 18 tap FIR filter with passband frequency of 10 kHz to 20 kHz and stopbands below 18 kHz and above 28 kHz.

In an example, one or more notch filters may be used to remove an AC lead detect signal. For example, a second order infinite impulse response (IIR) notch filter with notch center frequency of 2 kHz may be utilized.

One or more notch filters may be used to remove the respiration tone and other filters may be used to remove undesirable tones. In one example, such a filter may be a second order IIR filter having a programmable notch center frequency of 32/28.44444/25.6/23.27273 kHz. Also, a notch filter may be used to remove the front end chop frequency tone Accordingly, the filters can improve the signal-to-noise ratio of the analog ECG signal.

The ADC of the filter and ADC circuitry 108 converts the analog ECG signal into a digital ECG signal to provide to the pace pulse detection circuitry 110.

The pace pulse detection circuitry 110 analyzes data in the ECG signal to detect the presence of one or more pace pulses. For example, the pace pulse detection circuitry 110 detects a leading edge of a pace pulse in the ECG signal, validates the leading edge, observes the pace pulse, and validates the pace pulse, details of which are described below.

The pace pulse detector 102 uses the output interface 112 to transmit data related to the detected and validated pace pulses. The output interface 112 may transmit the data to other patient monitoring equipment such as the clinical ECG machine 114. The output interface can include hardware, such as a transmitter and related circuitry for wireless transfer of the data, or an interface that includes a connector for wired transfer of the data. In some examples, the clinical ECG machine 114 is used alongside other tests to help diagnose and monitor conditions affecting the heart. The clinical ECG machine 114 can be used to investigate symptoms of a possible heart problem, such as for example, chest pain, palpitations, dizziness, and/or shortness of breath.

FIG. 2 is a block diagram of an example implementation of the pace pulse detection circuitry 110 of the pace pulse detector 102 of FIG. In some examples, the pace pulse detection circuitry 110 is realized as a state machine. Different states of the state machine are described herein. The pace pulse detection circuitry 112 includes example leading edge detection circuitry 202, example transition time estimation circuitry 204, example leading edge validation circuitry 206, example pace pulse observation circuitry 208, example pace pulse validation circuitry 210, example pace word composition circuitry 212, example block window circuitry 214, example ringing window circuitry 216, example valid pace combination circuitry 218, and example external transmission circuitry 220.

Any or all of the pace pulse detection circuitry 112, the leading edge detection circuitry 202, the transition time estimation circuitry 204, the leading edge validation circuitry 206, the pace pulse observation circuitry 208, the pace pulse validation circuitry 210, the pace word composition circuitry 212, the block window circuitry 214, the ringing window circuitry 216, the valid pace combination circuitry 218, and/or the external transmission circuitry 220 of FIG. 2 may be instantiated (e.g., creating an instance of, bring into being for any length of time, materialize, implement, etc.) by programmable circuitry such as a central processor unit (CPU) executing first instructions. Additionally or alternatively, any or all of the circuitry 112 of FIG. 2 may be instantiated (e.g., creating an instance of, bring into being for any length of time, materialize, implement, etc.) by (i) an ASIC and/or (ii) a field programmable gate array (FPGA) structured and/or configured in response to execution of second instructions to perform operations corresponding to the first instructions. It should be understood that some or all of the circuitry of FIG. 2 may, thus, be instantiated at the same or different times. Some or all of the circuitry of FIG. 2 may be instantiated, for example, in one or more threads executing concurrently on hardware and/or in series on hardware. Moreover, in some examples, some or all of the circuitry of FIG. 2 may be implemented by microprocessor circuitry executing instructions and/or FPGA circuitry performing operations to implement one or more virtual machines and/or containers.

The leading edge detection circuitry 202 tracks the ECG signal over a pace edge observation window. In some examples, the pace edge observation window is 16 clocks. In some examples, each clock is equivalent to approximately 125 µs. In other examples, other durations for pace edge observation windows are used including, for example, eight clocks, four clocks, etc. The number of clocks over which the change in the ECG signal is tracked is programmable using, for example, a register control T_OBS_PACE_EDGE.

The leading edge detection circuitry 202 tracks or determines the change in amplitude (ΔA) of the ECG signal over the pace edge observation window. The leading edge detection circuitry 202 compares the amplitude change to an amplitude change threshold ($\Delta A_{THR}$). The amplitude change threshold can be programmed using, for example, a register control AD_EDGE_THR_REG. In some examples, the amplitude change threshold is 300 µV. In some examples, the amplitude change threshold is a value between 10 µV and 700 mV. In other examples, other values may be used. If the change in amplitude satisfies, e.g., exceeds, the amplitude change threshold, then the state machine or the pace pulse detection circuitry 112 transitions to a leading edge validation process to validate that the detected leading edge is a leading edge of a pace pulse.

Figure 3:
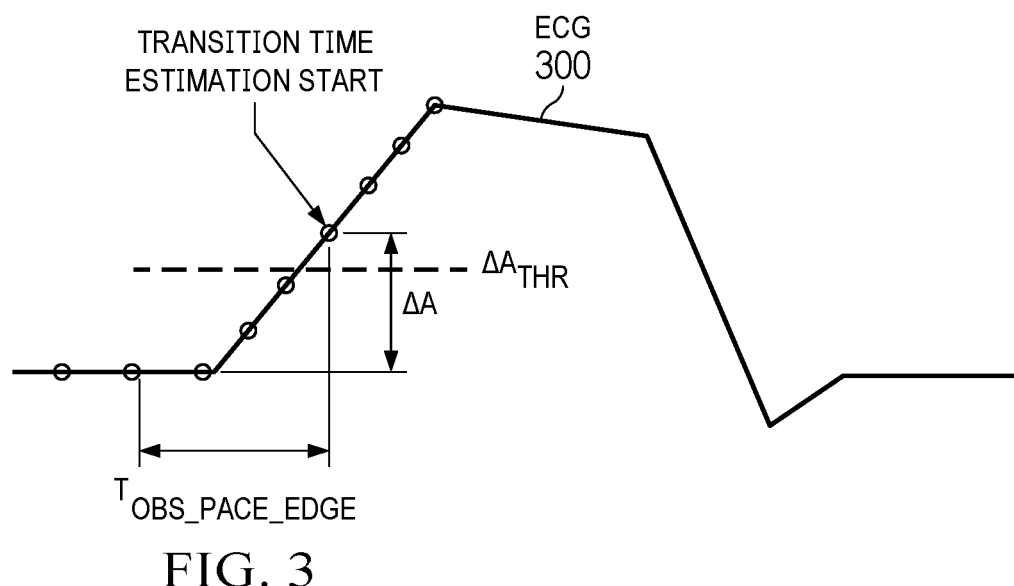
FIG. 3 is a graph illustrating an example of leading edge detection.

FIG. 3 is a graph illustrating an example of leading edge detection in an ECG signal 300. In this example, the leading edge detection circuitry 202 determines that the amplitude change (ΔA) of the ECG signal 300 crosses the amplitude change threshold ($\Delta A_{THR}$) at a time within a pace edge observation window ($T_{OBS\_PACE\_EDGE}$).

The transition time estimation circuitry 204 computes the transition time of the leading edge. For example, the transition time estimation circuitry 204 calculates ratios of amplitude change over a N number of clocks ($N_{TR}$). N may be a different number of clocks (e.g., 1, 2, 4, 8, 12, 16). The ratios are referred to as slope ratios. The ratios are programmable using, for example, registers SR_THR_2_TO_1, SR_THR_4_TO_2, SR_THR_8_TO_2, SR_THR_8_TO_4, SR_THR_12_TO_4, and SR_THR_16_TO_8. FIG. 3 shows an example in which the transition time estimating begins at the end of the pace edge observation window ($T_{OBS\_PACE\_EDGE}$). The transition times are used to validate the leading edge as disclosed herein.

The leading edge validation circuitry 206 determines a metric based on the amplitude changes and the transition times. For example, the leading edge validation circuitry 206 determines a metric referred to as a Figure of Merit (FOM). A FOM is a ratio of a change in amplitude over the transition time. A respective FOM is determined for each of the different $N_{TR}$ number of clocks. The FOMs are compared to a FOM threshold. The FOM threshold is represented by a reference model or mask of the amplitude change versus transition time. The leading edge validation circuitry 206 monitors the FOMs and determines if or when a FOM has satisfied or exceeded a FOM threshold at a particular time or cycle.

Figure 4:
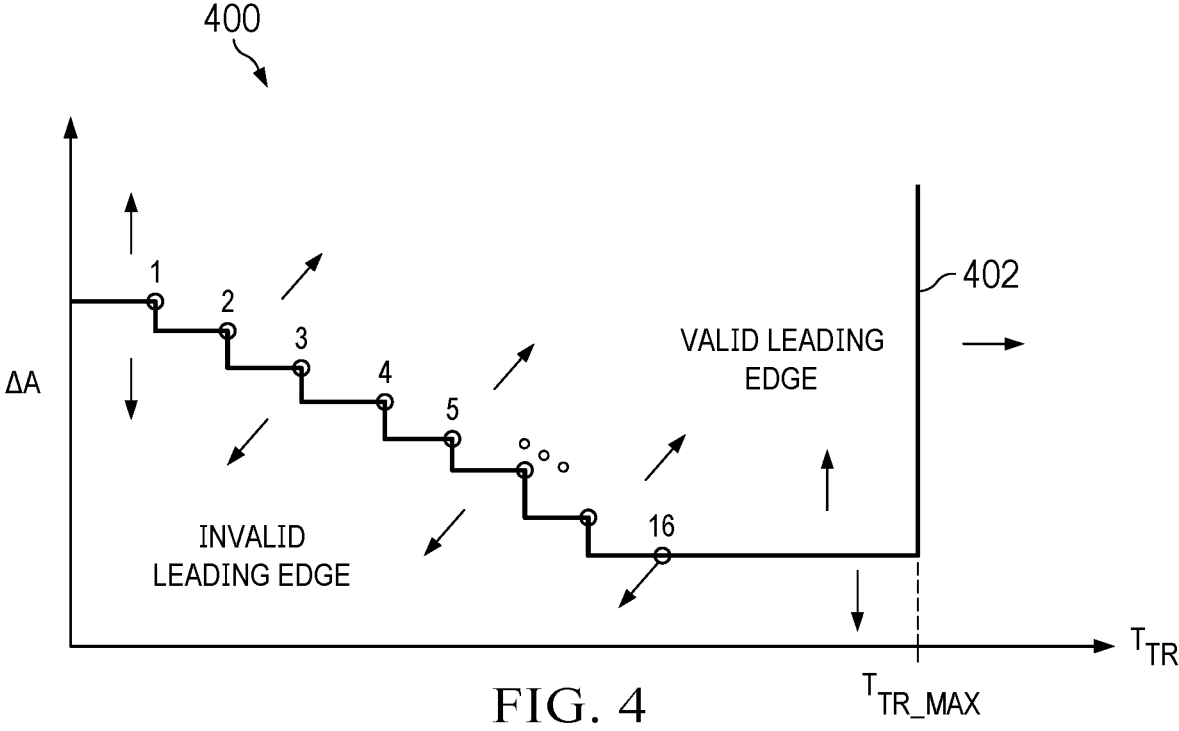
FIG. 4 is a graph of an example reference mask.

FIG. 4 is a graph of an example reference mask 400 of amplitude change versus transition time. The amplitude change on the y-axis is plotted against the transition time on the x-axis. Amplitude changes for transition times that fall above the plotted mask of the amplitude change versus transition time indicate a valid leading edge. Amplitude changes for transition times that fall below the plotted mask of the amplitude change versus transition time indicate an invalid leading edge.

In the example of FIG. 4, a greater amplitude change at clock cycle 1 is needed for the leading edge validation circuitry 206 to validate the leading edge of a pulse than the amplitude change at clock cycle 16. In this example, each clock cycle has a respective threshold (e.g., FOM threshold). For example, the amplitude changes are stepped down as time progresses. In other examples, the mask of the amplitude change versus transition time may be flat where the same amplitude change is used for each clock cycle. In still other examples, the mask of the amplitude change versus transition time may have other shapes. In some examples, the mask of the amplitude change versus transition time is programmable to define rules in such a way that a sharply rising transition in an ECG signal is required to have a larger amplitude to be detected as a valid edge as compared to a slower rising transition in an ECG signal. In the example of FIG. 4, the 16 points of ΔAmplitude for the mask of the amplitude change versus transition time are defined using the register controls FOM_THR_REGx (where x equals the clock cycle numbers 1 to 16).

Another way of viewing the mask of the amplitude change versus transition time of FIG. 4 is that the y axis represents the FOM threshold, and the x axis represents clock cycles. The mask of the amplitude change versus transition time shows the FOM threshold that is to be satisfied or exceeded at the respective clock cycles for the leading edge validation circuitry 206 to validate a leading edge of the pace pulse.

The vertical spike 402 in the mask of the amplitude change versus transition time of FIG. 4 is positioned at a maximum transition time, T_TR_MAX. The maximum transition time is a maximum time after which no amplitude change or FOM can satisfy the respective threshold. In other words, too much time has passed for a leading edge of a pace pulse to be detected.

After the leading edge validation circuitry 206 determines that a portion of the ECG signal is likely a leading edge (e.g., based on the FOM satisfying the FOM threshold at a clock cycle), the leading edge validation circuitry 206 continues to compare FOMs to respective FOM thresholds. To validate the leading edge, the leading edge validation circuitry 206 determines the computed FOM (ΔAmplitude over the computed transition time x) crosses a FOM threshold, reaches a peak, and then starts to fall.

The leading edge validation circuitry 206 identifies an end point of the leading edge as the point where the FOM goes below a level derived as a scaled value of the FOM threshold (FOM$_{THR}$), with the scale factor programmed using, for example, FOM_BASE_LVL_SCALE. The scaled value is programmable, for example, between 0 and 1.

Figure 5:
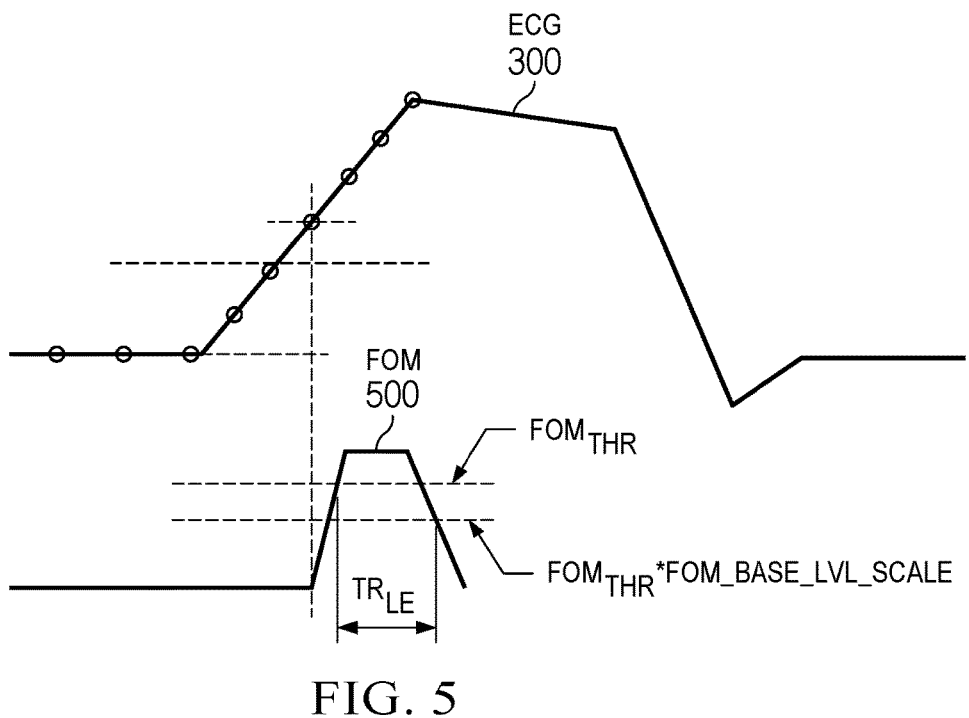
FIG. 5 is a graph illustrating an example of leading edge validation.

FIG. 5 is a graph illustrating an example of leading edge validation in which the end of the leading edge of the pace pulse is detected using the ECG signal 300 and a FOM plot 500. As shown in FIG. 5, there is a point at which the FOM falls below the FOM threshold (FOM$_{THR}$) by more than the scaled amount of the FOM threshold (FOM$_{THR}$*FOM_BASE_LVL_SCALE). Based on the point where the leading edge is detected and where the leading edge is determined as ended, the leading edge validation circuitry 206 computes the actual transition time. The actual transition time is represented in FIG. 5 as TR$_{LE}$. Minimum and maximum values of actual transition time for any valid edge (including the leading edge) are programmable. In some examples, the minimum and maximum values of actual transition time are programmable using register controls T_TR_MIN and T_TR_MAX, respectively.

When the leading edge validation circuitry 206 validates a leading edge of a pace pulse, the pace pulse observation circuitry 208 starts a pace pulse observation window. The duration of this window is programmable using, for example, register control T_OBS_PACE_WINDOW. During the pace pulse observation window, subsequent edges in the ECG are detected. The leading edge detection and leading edge validation operations are repeated to detect edges during the pace pulse observation window.

In some examples, during the pace pulse observation window, the amplitude threshold used for the leading edge detection is derived as the larger of two values: (1) the value as programmed in ΔA$_{TH}$ or (2) the largest peak amplitude change (ΔA$_{MAX}$) detected up to that point in the pace pulse observation window scaled by a factor DYN_AMPL_THR_SCALE. In addition, during the pace pulse observation window, the FOM threshold for the edge detection for edges after the leading edge is derived as the larger of two values: (1) the value as programmed in the mask of the amplitude change versus transition time or (2) the largest Peak FOM detected up to that point in the pace pulse observation window scaled by a factor DYN_FOM_THR_SCALE.

Additionally, in some examples, when the actual transition time exceeds a value programmed by parameter T_TR_

TIMEOUT, a time-out operation results. In a time-out operation, the pace pulse observation window is terminated. When the pace pulse observation window is terminated in a time-out operation, the pace pulse is analyzed based on all transitions or edges that happened from the first leading edge up to that point at which the time-out operation was triggered.

At the end of the pace pulse observation window, whether the window ended after a programmed duration or was truncated by a time-out operation, the pace pulse validation circuitry 210 validates the pace pulse. The pace pulse validation circuitry 210 analyzes the peaks of the FOM to determine the leading and trailing edge. The pace pulse validation circuitry 210 computes the pulse amplitude and the width (i.e., duration). The pace pulse validation circuitry 210 compares the detected or computed pulse amplitude and width against a programmed or reference model or mask of amplitude verses width to validate the pace pulse. In some examples, minimum and maximum widths are programmed using register controls T_PW_PACE_MIN and T_PW_PACE_MAX, respectively. In some examples, the amplitude and width for an 8-point mask are programmable using register controls AMPL_THR_PACE1 . . . 8 and T_PW_PACE1 . . . 8, respectively.

Figure 6:
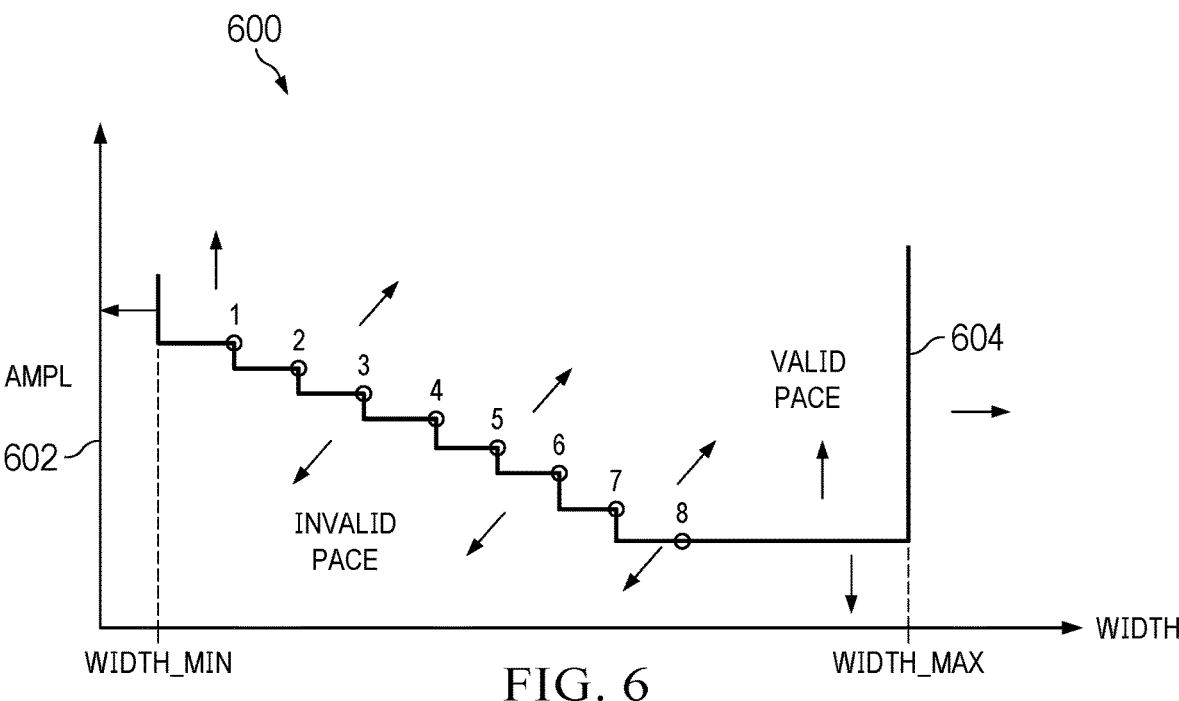
FIG. 6 is a graph of another example reference mask.

FIG. 6 is an example mask 600 of amplitude versus width. As shown, pulse amplitude along the y-axis is plotted against pulse width along the x-axis. Amplitude magnitudes for widths that fall above the plotted mask of the amplitude versus width time indicate a valid pulse. Amplitude magnitudes for width that fall below the plotted mask 600 of the amplitude versus width indicate an invalid pulse. In the example of FIG. 6, a greater amplitude magnitude at clock cycle 1 (e.g., at a relatively short width) is needed for the pace pulse validation circuitry 210 to validate the pace pulse than the amplitude magnitude at clock cycle 16 (e.g., at a relatively longer width). In this example, each clock cycle has a respective threshold, and the amplitude magnitudes are stepped down as the widths increase.

FIG. 6 shows a first vertical spike 602 in the mask 600 of the amplitude versus width at a minimum width, which sets a lower boundary for a duration of a pulse to be a valid pulse. FIG. 6 shows a second vertical spike 604 in the mask 600 of the amplitude versus width at a maximum width, which sets an upper boundary for a duration of a pulse to be a valid pulse. In other words, regardless of the amplitude, a pace pulse is not validated unless it has a duration at least as great as the minimum width. In addition, regardless of the amplitude, a pace pulse is validated if it has a duration that exceeds the maximum width. The values for the minimum width and/or the maximum width are programmable.

When a pace pulse is validated, the pace word composition circuitry 212 composes a pace word. In some examples, a pace word is composed with the amplitude and width of the pace pulse. In some examples, the pace word is a readout or digital signal of the properties of a pace pulse. In some examples, the pace pulse is transmitted with ECG frames. ECG frames are blocks or cycles of times within the ECG signal.

The pace pulse observation window is followed by a block window. In the block window, the block window circuitry 214 prevents or otherwise suspends detection of edges or transitions in an ECG signal. Pace pulses are separated by time. Thus, after a pace pulse is detected, there will not be another pace pulse for a period of time. Computing resources are conserved during the blocking window because the ECG signal is not being analyzed to detect a leading edge, trailing edge, and/or pace pulse. The blocking window duration or time in clocks for which edge detection is disabled is programmable. In some examples, the blocking window duration is set using register control T_W_BLOCK_DETECTION.

The block window is followed by a ringing window. In some examples, a notch filter used to remove the AC lead of detection creates a ringing for pace pulses with large amplitudes, which can last for a long time and be detected as false pulses. The ringing window helps prevent spurious detection (as pace pulses) of artifacts following a high amplitude pace pulse that could be created by the ring in the notch filters. During the ringing window, the ringing window circuitry 216 scales the thresholds used for leading edge detection through a scaling factor from the detected peaks of the most recently concluded pace pulse observation window. In some examples, the ringing window circuitry 216 programs the scaling factor. In some examples, the ringing window circuitry 216 identifies an amplitude change in the ECG signal during the ringing window and categorizes the amplitude change as a ringing artifact based on the scaled threshold.

In some examples, the ringing window circuitry 216 divides the ringing window into three ringing windows or sub-windows RW1, RW2, RW3. In some examples, the ringing window circuitry 216 programs the width of one or more of the respective sub-windows. In some examples, the ringing window circuitry 216 programs the widths of one or more of the sub-windows and/or the FOM thresholds used in leading edge detection by a scaling factor such that the widths of the respective sub-windows are different and/or the FOM thresholds are different. For example, a width of RW1 may be set using register controls T_W_RINGING_WINDOW1. Also, for deriving the FOM threshold, the largest FOM in the most recently concluded pace pulse observation window is scaled by a factor FOM_HYSTER-ESIS_FACTOR1. In some examples, similar controls are used for the other sub-windows, e.g., RW2 and RW3, respectively. In some examples, multiple windows are provided so that the thresholds can be reduced (e.g., increasingly scaled) as time passes. The ringing window prevents ringing artifacts and trailing edges from being detected as a new or subsequent pace pulse. In addition, adjacent pulses, such as with the example of biventricular pulses, can be detected as long as both the pulses have similar amplitude parameters.

Figure 7:
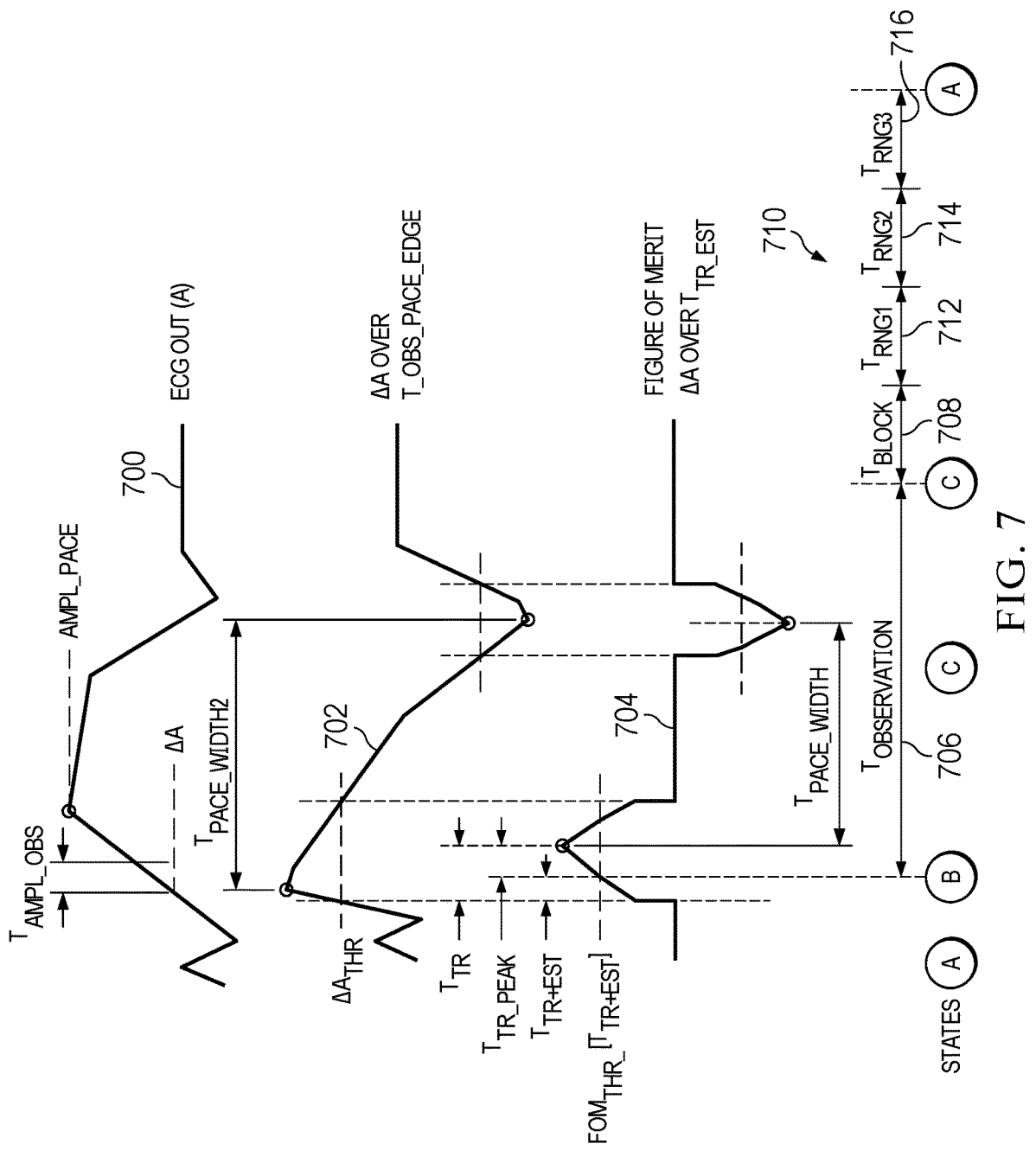
FIG. 7 is a graph of an example pace pulse detection timing.

FIG. 7 is a graph of an example pace pulse detection timing. FIG. 7 provides an overview of the pace pulse detection process. An ECG signal 700 is analyzed to detect a leading edge of a pace pulse and a width of the pace pulse 702. The leading edge is validated by analyzing FOMS 704, detect edges within a pace pulse observation window 706, and validate the pace pulse. In an example, FOMS analysis is carried out by determining T_TR_EST, which is the estimated rise time for the given edge. This is the initial estimated value that may be later qualified as a valid edge; however, initially it is not guaranteed that the pace has reached its highest point because the data is being processed in real time, so the pace may further continue to rise. In one example in which the pace edge continues to rise beyond the edge validation, the continued rise is recorded and after the edge is over, the actual rise time of the edge is determined, as denoted as T_TR_PEAK, which is the rise time until the peak of the FOMS 704. Based on the shape of the pulse in some cases T_TR_EST can be equal to T_TR_PEAK. After validation of a pace pulse, a block window 708 and ringing window 710 are observed. In this example, the ringing window is divided into three sub-windows 712, 714, 716.

If a valid pace event (i.e., pace pulse) is detected on any of a plurality of channels reading the ECG signal, pace pulse validation circuitry 210 generates a digital signal PACE_VALID_CHx (where x equals the channel number or identifier) that indicates the valid pace pulse. For example, the pace pulse validation circuitry 210 can generate a high signal or 1 for that channel, which stays high until the end of that ECG frame. The valid pace pulse combination circuitry 218 combines the PACE_VALID_CHx signals across the channels to create a single PACE_VALID signal. The single PACE_VALID signal can be used to generate an interrupt on a general-purpose input/output (GPIO) pin.

Figure 8:
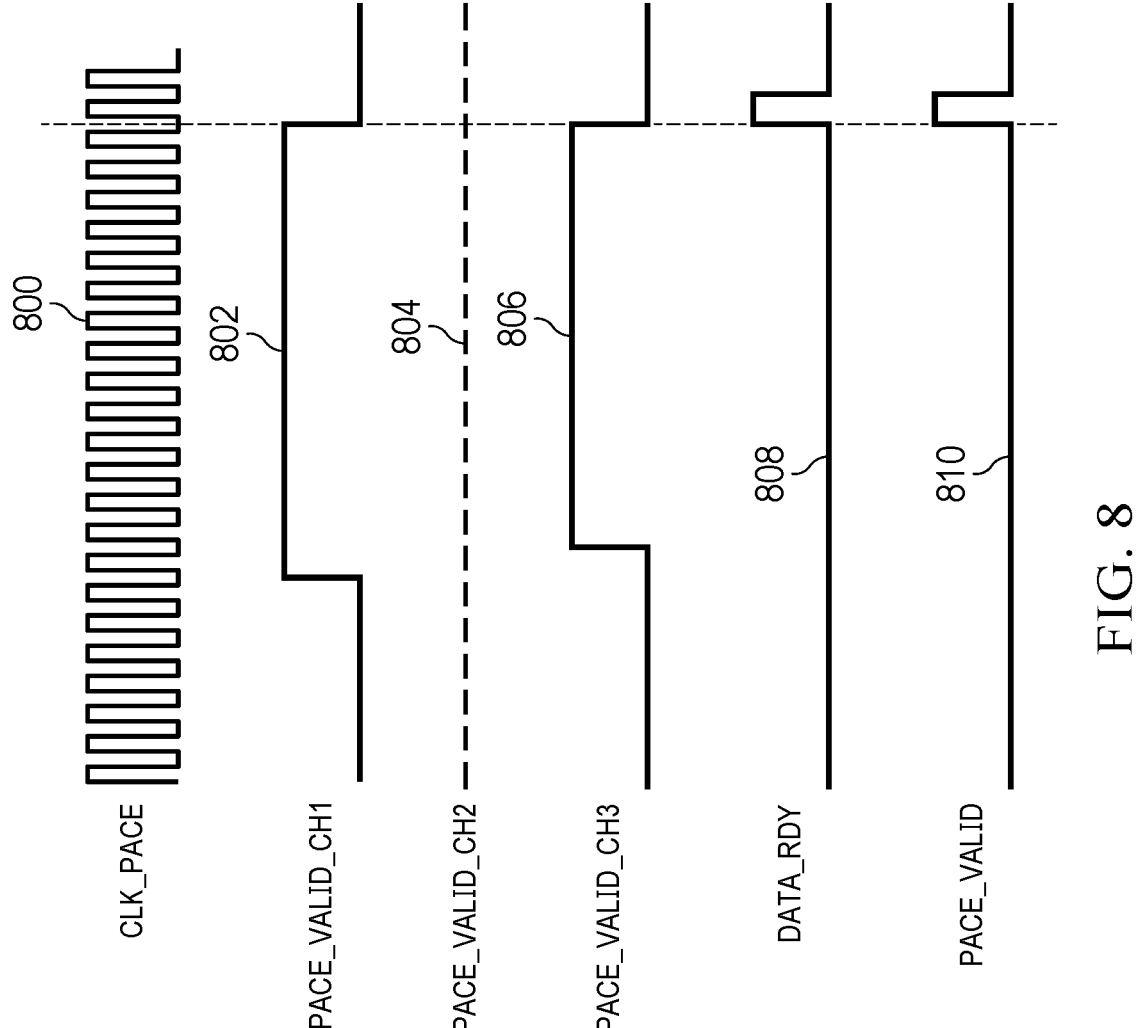
FIG. 8 is a graph of an example valid pace pulse combination.

FIG. 8 is a graph of an example valid pace pulse combination. FIG. 8 shows a clock signal 800. FIG. 8 also shows a first digital signal 802 generated by the pace pulse validation circuitry 210 for a first channel, a second digital signal 804 generated by the pace pulse validation circuitry 210, and a third digital signal 806 generated by the pace pulse validation circuitry 210. In other examples, there may be more or fewer channels. FIG. 8 also shows a data ready signal 808, used to prompt combination of the valid pace pulse signals.

In this examples signals PACE_VALID_CH1 . . . 3 802, 804, 806 are combined to a single PACE_VALID signal 810 based on the number of valid pace pulse detections as specified by a register control NUM_PACE_VALID_COM-BINE. For example, a valid pace pulse is confirmed if any one, any two, and/or all (or more) of the channels record a valid pace pulse. The PACE_VALID signal from different channels could come at slightly offset frames. A register control such as WINDOW_PACE_VALID_COMBINE can be used to define an observation window (in terms of number of ECG frames) for the plurality (e.g., four) of channels. If for example, register control NUM_PACE_VALID_COMBINE is set to two and register control WINDOW_PACE_VALID_COMBINE is set to one, then the following event results in a PACE_VALID signal getting generated in Frame 2:

Frame 1: PACE_VALID_CH1 goes high
Frame 2: PACE_VALID_CH2 goes high
As noted above, FIG. 8 is a graph of an example valid pace pulse combination that shows the combination of signals that indicate valid pace pulses from multiple channels into a single pace pulse valid signal. The single pace pulse valid signal 800 can be used to trigger an interrupt to indicate to the MCU that a pace pulse has been found on at least one of the channels.

The external transmission circuitry 220 outputs data related to the pace pulses and ECG signal via, for example, the output interface 112 of the pace pulse detector 102. The external transmission circuitry 220 can output data from any or all the channels to a memory such as a first in first out (FIFO) buffer. For example, external transmission circuitry 220 outputs data from the pace pulse channels onto a Pace FIFO by setting a register control EXT_OUT_EN_PACE_CHx (where x is the channel number or identifier). In some examples, the two least significant bits of a 24-bit pace pulse channel data is the channel number. In some examples, there are two modes for how the external transmission circuitry 220 writes pace pulse output data into the PACE FIFO (or other memory). The two modes are Always-Transmit Pace mode and Active-Transmit Pace mode.

In some examples, in the Always-Transmit Pace mode, the external transmission circuitry 220 continuously writes unmasked DATA_PACE_CH1 . . . 4 data into the PACE FIFO. The unmasked data from these channels is raw data that has not been analyzed against the mask described above.

In some examples, the external transmission circuitry 220 continuously writes the data at the rate of clock pace, CLK_PACE.

In some examples, in the Active-Transmit Pace mode, the external transmission circuitry 220 transmits data only when the leading edge validation circuitry 206 identifies a valid leading edge of a pace pulse. Thus, in some examples, the unmasked DATA_PACE_CH1 . . . 4 streams are gated by an external pace window (EXT_PACE_WINDOW) defined around an internally detected event (e.g., a leading edge validation). The Active-Transmit Pace mode allows a gating of the external pace transmission based on internal detection and significantly reduces the payload of data that is throughput to an MCU (for instance included in the clinical ECG machine 114) to analyze pace events. The length of the external pace window (e.g., EXT_PACE_WINDOW) is programmable.

In some examples, a register bit PACE_EXT_ACTIVE_TX_EN changes the mode for the external transmission circuitry 220 to transmit data in the Active-Transmit Pace mode. In some examples, in the Active-Transmit Pace mode, the external transmission circuitry 220 writes the pace pulse data at 128 Kilosamples per second (ksps) with no data rate control into the PACE FIFO during the external pace window (EXT_PACE_WINDOW). Respective ones of the internal pace pulse detect channel (when enabled) generate a signal EXT_WINDOW_PACEx (where x equals the channel number or identifier). In some examples, the EXT_PACE_WINDOWx signals stretch 32 samples to the left ($t_{PRE\_LE}$) and a programmable number of samples to the right ($t_{POST\_LE}$) programmed by DELAY_EXT_PACE_WINDOW_END) of the pace pulse observation window.

Figure 9:
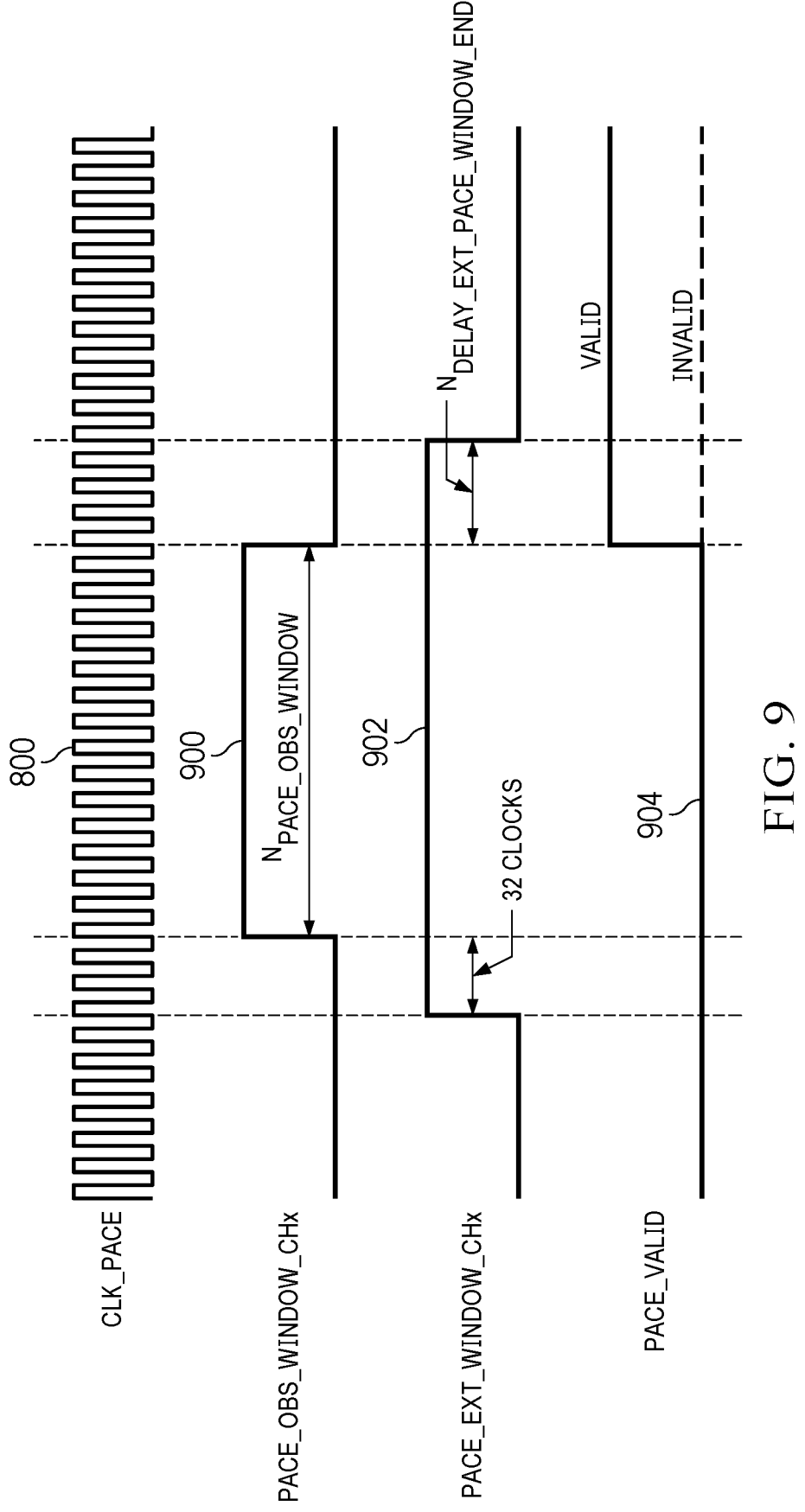
FIG. 9 is a graph of an example timing for an example active-transmit pace mode.

FIG. 9 is a graph of an example timing for an example active-transmit pace mode. FIG. 9 shows the clock pace 800, a pace observation window signal for x number of channels 900, a pace external window signal for x number of channels 902, and a pace valid signal 904. The PACE_EXT_WINDOW 902 represents a window during which the high speed pace data is transmitted so that an FPGA or micro-controller can carry out the pace detection externally (e.g., off-chip). PACE_EXT_WINDOW is a window defined around the PACE_OBS_WINDOW, which is identified as the likely window of a pace pulse. N_DELAY_EXT_PACE_WINDOW_END represents additional stretching of the external pace window beyond the internal pace window to give off-chip processing (e.g., an FPGA or micro-controller) a bit of extra data for detection.

The valid pace pulse combination circuitry 220 can combine the signals to create a single EXT_PACE_WINDOW signal (e.g., pace external window signal for x number of channels 902) that is used by the external transmission circuitry 220 for gating the external pace pulse transmission. For example, the signals from channels EXT_PACE_WINDOW_CH1 . . . 4 may be combined using an OR operation to create the EXT_PACE_WINDOW signal using a register control, for example, EXT_PACE_WINDOW_COMBINEZx (where x equals the channel number or identifier). The internal pace pulse detect channels participate in the definition of the external pace window for active transmit. For example, the internal pace pulse detect channel x (if enabled), participates in the definition of the external pace window based on the signal EXT_PACE_WINDOW_COMBINEZx. If the EXT_PACE_WINDOW_COMBINEZx bit is 1, then the signal EXT_PACE_WINDOW_CHx is used in the OR operation to generate the signal EXT_PACE_WINDOW. If the EXT_PACE_WINDOW_COMBI- NEZx bit is 0, then the signal EXT_PACE_WINDOW_COMBINEZx is left out from the OR operation.

Figure 10:
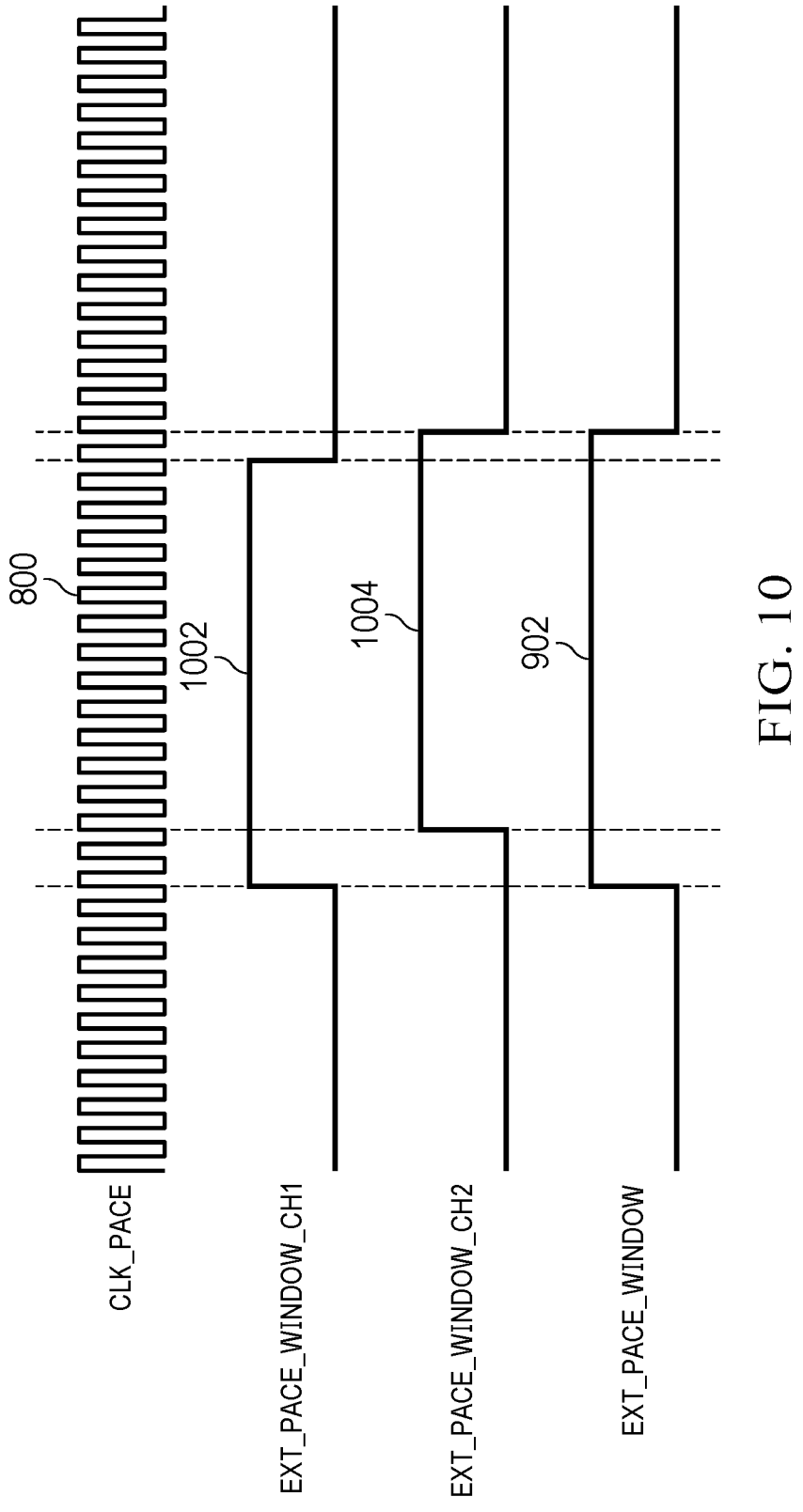
FIG. 10 is a graph of an example combining of pace pulse windows of different channels into a single window.

FIG. 10 is a graph of an example combining of pace pulse windows of different channels into a single window. FIG. 10 shows the clock pace 800, a pace external window signal for a first channel 1002, a pace external window signal for a second channel 1004, and the combined pace external window signal for x number of channels 902.

In some examples, the leading edge detection circuitry 202, the transition time estimation circuitry 204, the leading edge validation circuitry 206, the pace pulse observation circuitry 208, the pace pulse validation circuitry 210, the pace word composition circuitry 212, the block window circuitry 214, the ringing window circuitry 216, the valid pace pulse combination circuitry 218, the external transmission circuitry 220, and/or the pace pulse detection circuitry 112 is instantiated by programmable circuitry executing pace pulse detection instructions and/or configured to perform operations such as those represented by one or more of the flowchart(s) of FIGS. 12-19.

Figure 11A:
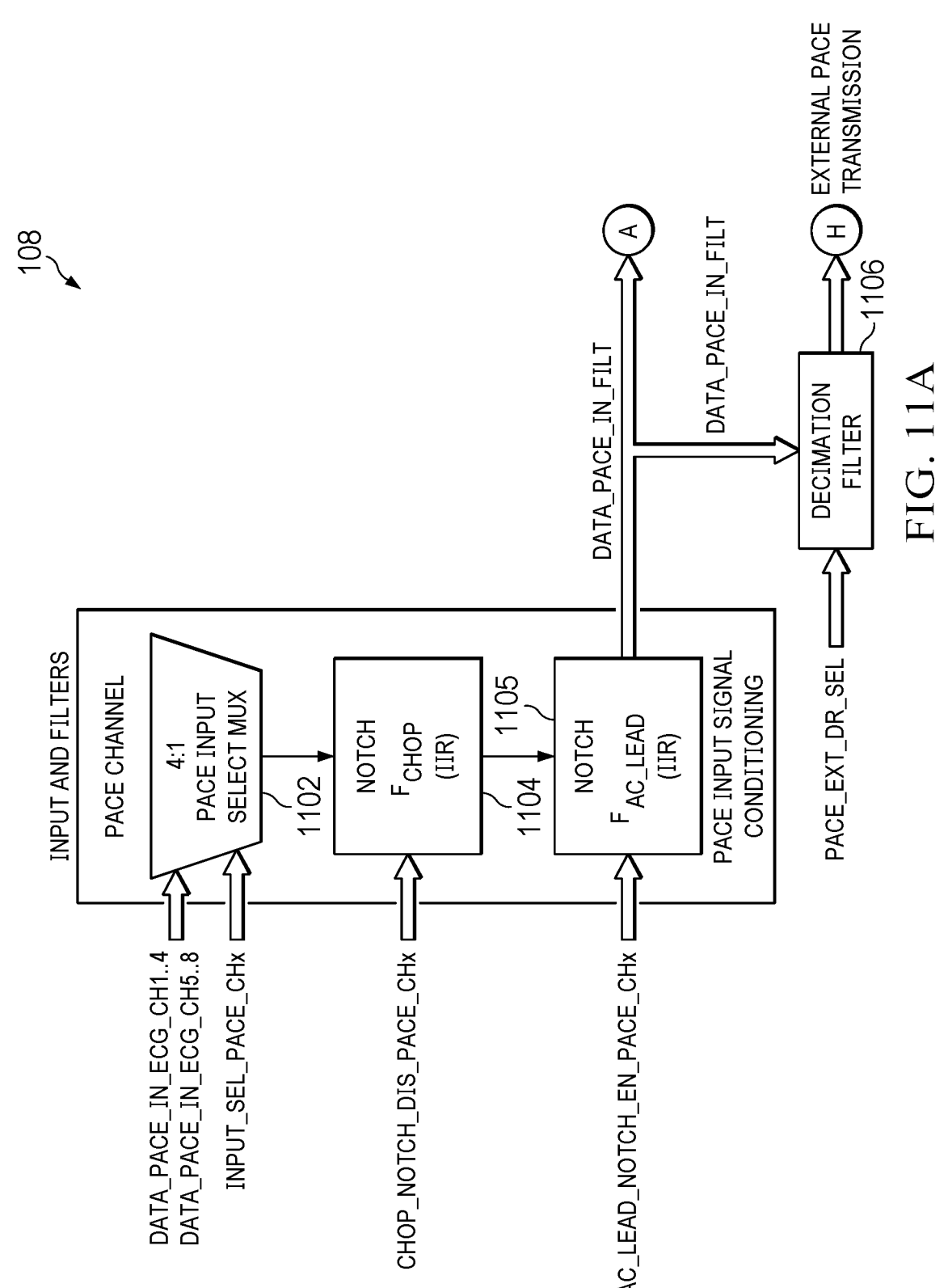
FIGS. 11A-11C form a schematic diagram of an example implementation of the pace pulse detector of FIG. 1.
Figure 11B:
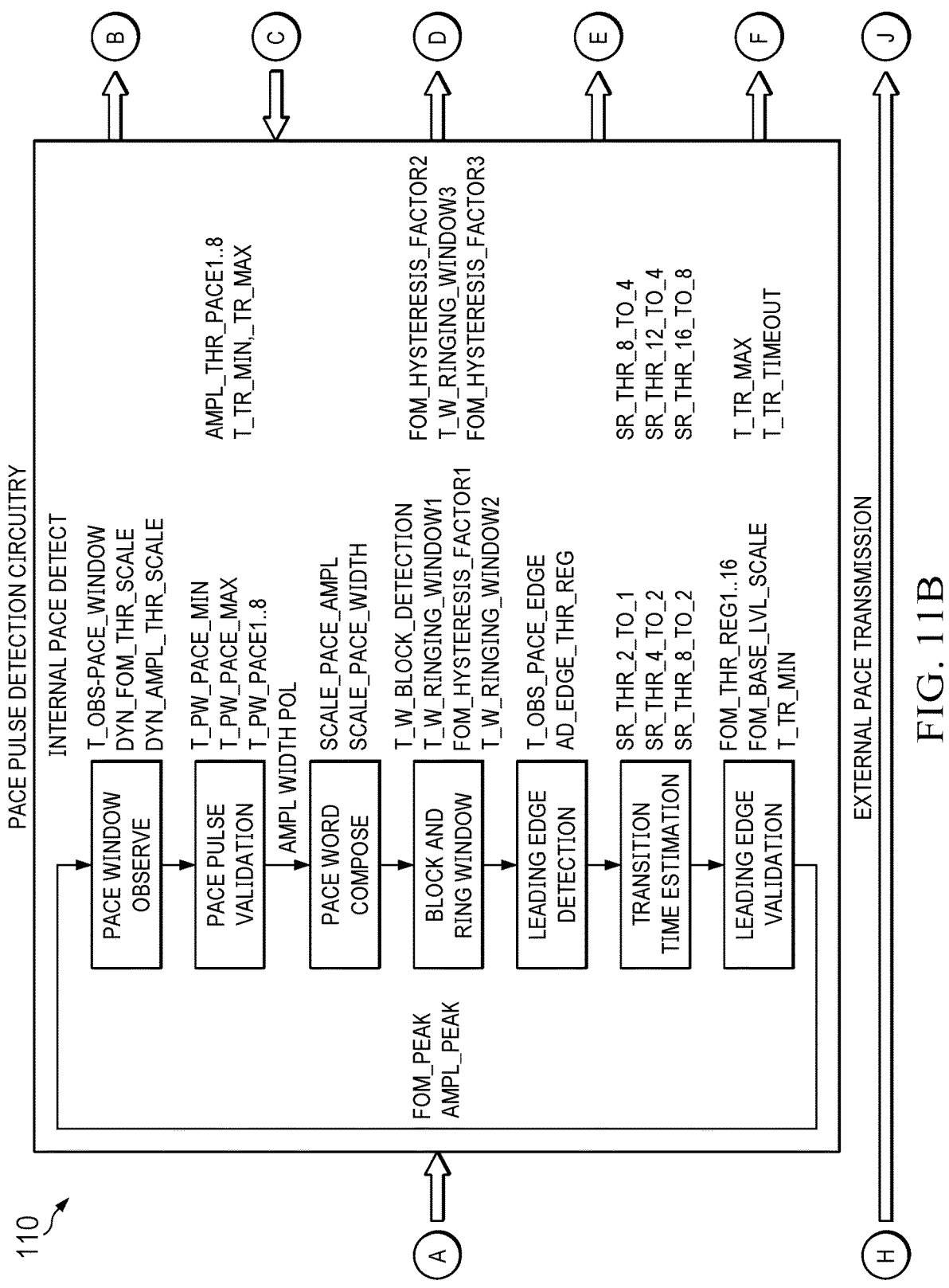
Figure 11C:
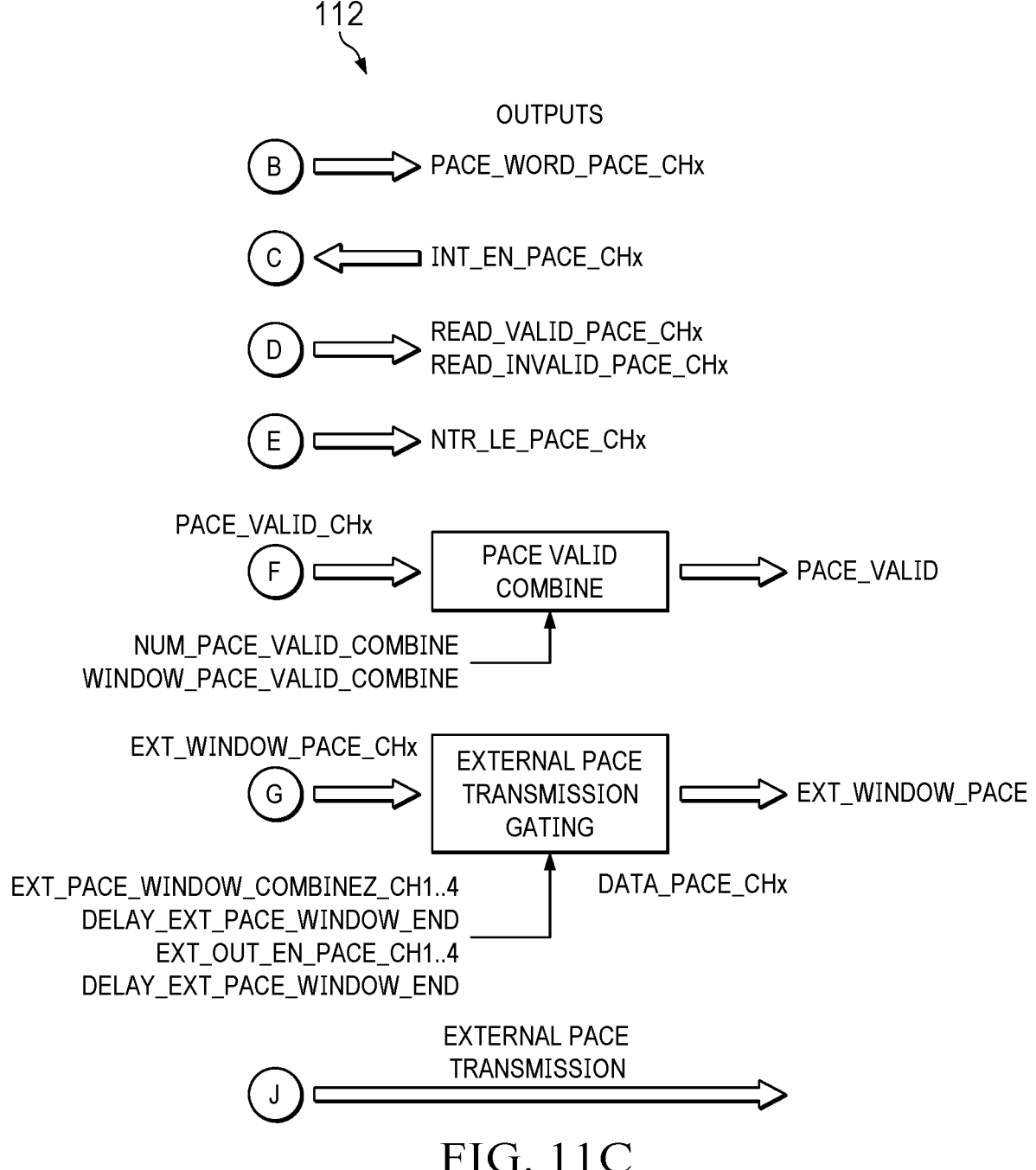

FIGS. 11A-11C form a schematic diagram of an example implementation of the pace pulse detector 102 of FIG. 1. In the illustrated example, the pace pulse detector 102 includes the filters 108 to perform input signal conditioning (FIG. 11A). The example filters 108 include an example Pace input select MUX 1102, one or more example notch filters 1104, 1105, and an example decimation filter 1106. Other examples may include more or fewer signal conditioning components. The example input signal conditioning includes filtering to remove in-band tones from the signal band of the pace pulse. In some examples, the input signal conditioning includes the analog-to-digital converter (ADC) output from the ECG channels being low-pass filtered using, for example, an ECG low pass filter (LPF) to form the input for the pace channels. In some examples, a corner of the LPF can be set to either 10 kHz or 20 kHz. In some examples, the pace pulse can have some interference from artifacts at a chopping frequency of the input A (ECG INA) as well as from the excitation used for the AC lead detect. Notch filters 1104 can be used to reject these artifacts so that the artifacts do not cause spurious pace detection.

In some examples, the decimation filter 1106 reduces the rate of data sampling. ECG data is at a lower frequency than the rate of data sampling, and the decimation filter 1106 enables reading of data more slowly. For example, the decimation filter can enable a reduction from one million samples/sec to 128 ksps or 64 ksps, etc. The decimation filter 1106 also improves the signal-to-noise ratio.

The pace pulse detector 102 includes the pace pulse detection circuitry 110 to operate in accordance with this disclosure (FIG. 11B). The pace pulse detector 102 also includes data outputs of the output circuitry 112 (FIG. 11C). In the example of FIGS. 11A-C, the valid pace pulse combination circuitry 218 and the external transmission circuitry 220 may be part of the or combined with the output circuitry 112. As disclosed herein, different rearrangements and combinations of the elements of FIG. 2 may be made. Also, in some examples, data from one or more of the pace channels can either be input to the internal pace detect block (i.e., the pace pulse detection circuitry 110), and/or the data from the one or more pace channels can be streamed from the input filters 108 to into a memory such as, for example, the pace FIFO for external transmission.

The pace pulse detection circuitry 112 may implement one or more algorithms for calculating, computing, or otherwise determining amplitude and/or FOM thresholds. For example, a FOM threshold may be determined by Equation (1).

$$FoM_{THR(N_{TR_{EST}})}=Max\{K_{RING_x}*FoM_{PEAK\_HIST\_PREV},$$
$$\Delta A_{THR}(N_{TR_{EST}}),FoM_{PEAK\_HIST\_CURR\_SAME},$$
$$FoM_{PEAK\_HIST\_CURR\_OPP}*K_{THR\_START}\}$$  Equation (1)

where $K_{RING_x}$ is a hysteresis factor corresponding to the respective window (FOM_HYSTERISIS_FACTORx). In states other than ringing state, $K_{RING_x}=0$.

where $FoM_{PEAK\_HIST\_PREV}$ is a peak value of FOM corresponding to the leading edge polarity found in the previous observation window.

where $\Delta A_{THR}(N_{TR_{EST}})=FOM\_THR(N)$ and is the FOM threshold set by the user for each value of NTR. In some examples, the FOM threshold can be set up to 16 different values.

where $N_{TR_{EST}}$ is the estimated rise time. When the sub finite state machine (sub fsm) is in state 1, $N_{TR_{EST}}=NTR$ calculated. When sub fsm is in state 2, $N_{TR_{EST}}=NTR$ [current lead edge].

where $FoM_{PEAK\_HIST\_CURR\_SAME}$ is a maximum value of the peak FOMs having same polarity as the current edge within the current observation window.

where $FoM_{PEAK\_HIST\_CURR\_OPP}$ is a maximum value of the peak FOMs having opposite polarity as the current edge within the current observation window.

In some examples, amplitude thresholds may be determined by Equation (2) and/or Equation (3).

$$\Delta A_{THR\_OBS}=Max\{K_{RING_x}*FoM_{PEAK\_HIST\_SREV},$$
$$\Delta A_{THR\_DEF}\}$$  Equation (2)

where $\Delta A_{THR\_DEF}$ is same as AD_EDGE_THR_REG, which is a threshold for starting computation of deltas, slope thresholds etc. when the main finite state machine (main FSM) is in state A or E.

$$\Delta A_{THR\_SUB\_OBS}=Max\{K_{RING_x}FoM_{PEAK\_HIST\_PREV},$$
$$\Delta A_{THR\_DEF},K_{THR\_AMPL}*FoM_{PEAK\_CONCLUDED}\}$$  Equation (3)

where $\Delta A_{THR\_SUB\_OBS}$ is a threshold for starting computation of deltas, slope thresholds etc. When the main FSM is in state B and the sub fsm is in state 1.

where $FoM_{PEAK\_CONCLUDED}$ is the peak value of FOM of the most recently concluded pace pulse edge.

While an example manner of implementing the pace pulse detection circuitry 112 of FIG. 1 is illustrated in FIG. 2, one or more of the elements, processes, and/or devices illustrated in FIG. 2 may be combined, divided, re-arranged, omitted, eliminated, and/or implemented in any other way. Further, the leading edge detection circuitry 202, the transition time estimation circuitry 204, the leading edge validation circuitry 206, the pace pulse observation circuitry 208, the pace pulse validation circuitry 210, the pace word composition circuitry 212, the block window circuitry 214, the ringing window circuitry 216, the valid pace pulse combination circuitry 218, the external transmission circuitry 220, and/or, more generally, the pace pulse detection circuitry 112 of FIG. 2, may be implemented by hardware alone or by hardware in combination with software and/or firmware. Thus, for example, any of the leading edge detection circuitry 202, the transition time estimation circuitry 204, the leading edge validation circuitry 206, the pace pulse observation circuitry 208, the pace pulse validation circuitry 210, the pace word composition circuitry 212, the block window circuitry 214, the ringing window circuitry 216, the valid pace pulse combination circuitry 218, the external transmission circuitry 220, and/or, more generally, the pace pulse detection circuitry 112, could be implemented by programmable circuitry in combination with machine readable instructions (e.g., firmware or software), processor circuitry, analog circuit(s), digital circuit(s), logic circuit(s), programmable processor(s), programmable microcontroller(s), graphics processing unit(s) (GPU(s)), digital signal processor(s) (DSP(s)), ASIC(s), programmable logic device(s) (PLD(s)), and/or field programmable logic device(s) (FPLD(s)) such as FPGAs. Further still, the example pace pulse detection circuitry 112 of FIG. 2 may include one or more elements, processes, and/or devices in addition to, or instead of, those illustrated in FIG. 2, and/or may include more than one of any or all of the illustrated elements, processes and devices.

Flowchart(s) representative of example machine readable instructions, which may be executed by programmable circuitry to implement and/or instantiate the pace pulse detection circuitry 112 of FIG. 2 and/or representative of example operations which may be performed by programmable circuitry to implement and/or instantiate the pace pulse detection circuitry 112 of FIG. 2, are shown in FIGS. 12-19. The machine readable instructions may be one or more executable programs or portion(s) of one or more executable programs for execution by programmable circuitry such as the programmable circuitry 2012 shown in the example processor platform 2000 discussed below in connection with FIG. 20 and/or may be one or more function(s) or portion(s) of functions to be performed by the example programmable circuitry (e.g., an FPGA) discussed below in connection with FIGS. 21 and/or 22. In some examples, the machine readable instructions cause an operation, a task, etc., to be carried out and/or performed in an automated manner in the real world. As used herein, "automated" means without human involvement.

The program may be embodied in instructions (e.g., software and/or firmware) stored on one or more non-transitory computer readable and/or machine readable storage medium such as cache memory, a magnetic-storage device or disk (e.g., a floppy disk, a Hard Disk Drive (HDD), etc.), an optical-storage device or disk (e.g., a Blu-ray disk, a Compact Disk (CD), a Digital Versatile Disk (DVD), etc.), a Redundant Array of Independent Disks (RAID), a register, ROM, a solid-state drive (SSD), SSD memory, non-volatile memory (e.g., electrically erasable programmable read-only memory (EEPROM), flash memory, etc.), volatile memory (e.g., Random Access Memory (RAM) of any type, etc.), and/or any other storage device or storage disk. The instructions of the non-transitory computer readable and/or machine readable medium may program and/or be executed by programmable circuitry located in one or more hardware devices, but the entire program and/or parts thereof could alternatively be executed and/or instantiated by one or more hardware devices other than the programmable circuitry and/or embodied in dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a human and/or machine user) or an intermediate client hardware device gateway (e.g., a radio access network (RAN)) that may facilitate communication between a server and an endpoint client hardware device. Similarly, the non-transitory computer readable storage medium may include one or more mediums. Further, although the example program is described with reference to the flowchart(s) illustrated in FIGS. 12-19, many other methods of implementing the example pace pulse detection circuitry 112 may alternatively be used. For example, the order of execution of the blocks of the flowchart(s) may be changed, and/or some of the blocks described may be changed, eliminated, or combined. Additionally or alternatively, any or all of the blocks of the flow chart may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The programmable circuitry may be distributed in different network locations and/or local to one or more hardware devices (e.g., a single-core processor (e.g., a single core CPU), a multi-core processor (e.g., a multi-core CPU, an XPU, etc.)). For example, the programmable circuitry may be a CPU and/or an FPGA located in the same package (e.g., the same integrated circuit (IC) package or in two or more separate housings), one or more processors in a single machine, multiple processors distributed across multiple servers of a server rack, multiple processors distributed across one or more server racks, etc., and/or any combination(s) thereof.

The machine readable instructions described herein may be stored in one or more of a compressed format, an encrypted format, a fragmented format, a compiled format, an executable format, a packaged format, etc. Machine readable instructions as described herein may be stored as data (e.g., computer-readable data, machine-readable data, one or more bits (e.g., one or more computer-readable bits, one or more machine-readable bits, etc.), a bitstream (e.g., a computer-readable bitstream, a machine-readable bitstream, etc.), etc.) or a data structure (e.g., as portion(s) of instructions, code, representations of code, etc.) that may be utilized to create, manufacture, and/or produce machine executable instructions. For example, the machine readable instructions may be fragmented and stored on one or more storage devices, disks and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of computer-executable and/or machine executable instructions that implement one or more functions and/or operations that may together form a program such as that described herein.

In another example, the machine readable instructions may be stored in a state in which they may be read by programmable circuitry, but require addition of a library (e.g., a dynamic link library (DLL)), a software development kit (SDK), an application programming interface (API), etc., in order to execute the machine-readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable, computer readable and/or machine readable media, as used herein, may include instructions and/or program(s) regardless of the particular format or state of the machine readable instructions and/or program(s).

The machine readable instructions described herein can be represented by any past, present, or future instruction language, scripting language, programming language, etc. For example, the machine readable instructions may be represented using any of the following languages: C, C++, Java, C #, Per, Python, JavaScript, HyperText Markup Language (HTML), Structured Query Language (SQL), Swift, etc.

As mentioned above, the example operations of FIGS. 12-19 may be implemented using executable instructions (e.g., computer readable and/or machine readable instructions) stored on one or more non-transitory computer readable and/or machine readable media. As used herein, the terms non-transitory computer readable medium, non-transitory computer readable storage medium, non-transitory machine readable medium, and/or non-transitory machine readable storage medium are expressly defined to include any type of computer readable storage device and/or storage disk and to exclude propagating signals and to exclude transmission media. Examples of such non-transitory computer readable medium, non-transitory computer readable storage medium, non-transitory machine readable medium, and/or non-transitory machine readable storage medium include optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms "non-transitory computer readable storage device" and "non-transitory machine readable storage device" are defined to include any physical (mechanical, magnetic and/or electrical) hardware to retain information for a time period, but to exclude propagating signals and to exclude transmission media. Examples of non-transitory computer readable storage devices and/or non-transitory machine readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer-readable instructions, machine-readable instructions, etc.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements, or actions may be implemented by, e.g., the same entity or object. Additionally, although individual features may be included in different examples or claims, these may possibly be combined, and the inclusion in different examples or claims does not imply that a combination of features is not feasible and/or advantageous.

FIG. 12 is a flowchart representative of example machine readable instructions and/or example operations 1200 that may be executed, instantiated, and/or performed by programmable circuitry to validate a pace pulse. The example machine-readable instructions and/or the example operations 1200 of FIG. 12 include the leading edge detection circuitry 202 identifying a leading edge of a pace pulse (block 1202). The transition time estimate circuitry 204 estimates a transition time based on the identified leading edge (block 1204). The leading edge validation circuitry 206 validates the leading edge (block 1206). The pace pulse validation circuitry 210 identifies a trailing edge of the pace pulse (block 1208). In addition, the pace pulse validation circuitry 210 determines a width of the pace pulse based on the leading edge and the trailing edge (block 1210). The pace pulse validation circuitry 210 validates the pace pulse based on the width (block 1212).

FIG. 13 is a flowchart representative of example machine readable instructions and/or example operations 1300 that may be executed, instantiated, and/or performed by programmable circuitry to observe a ringing window. The example machine-readable instructions and/or the example operations 1300 of FIG. 13 include the leading edge detection circuitry 202 identifying a leading edge of a pace pulse (block 1302). The pace pulse validation circuitry 210 identifies a trailing edge of the pace pulse (block 1304). In addition, the pace pulse validation circuitry 210 determines a width of the pace pulse based on the leading edge and the trailing edge (block 1306). The pace pulse validation circuitry 210 validates the pace pulse based on the width (block 1308). The ringing window circuitry 216 observes a ringing window after the pace pulse (block 1310).

Figure 14:
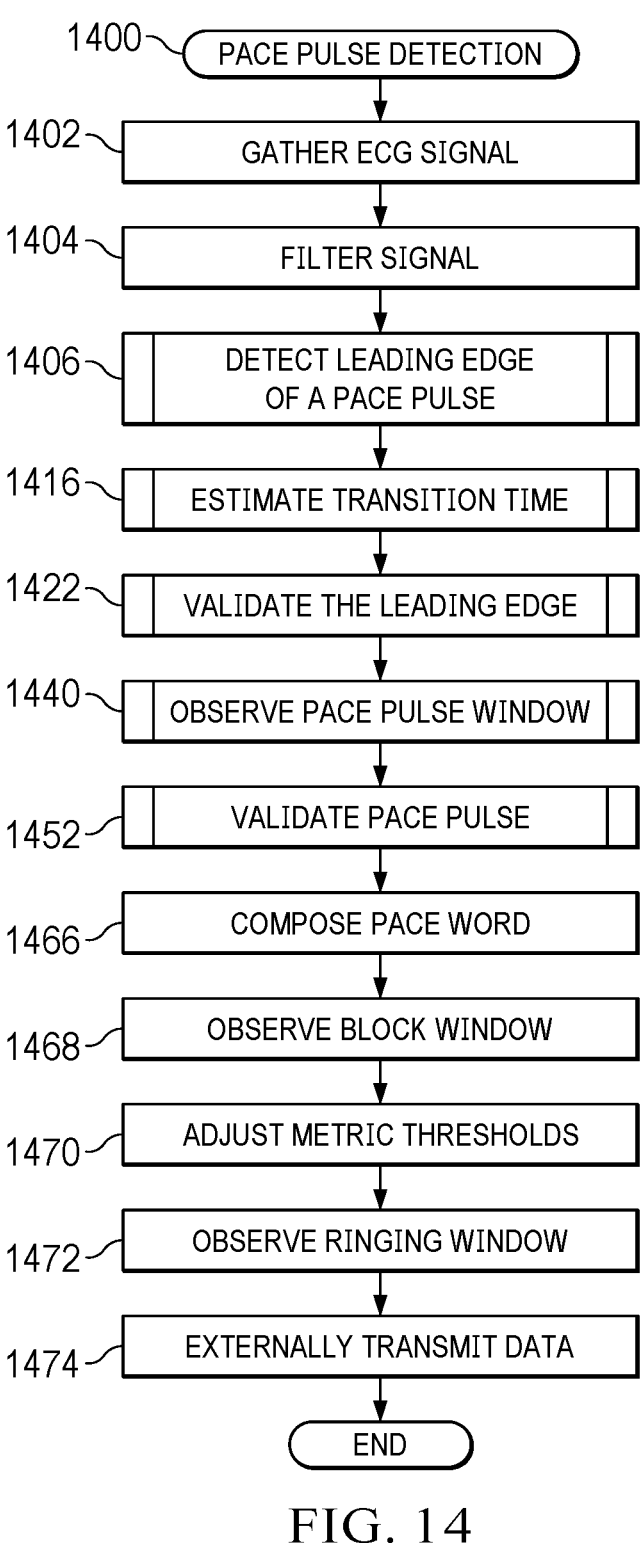

FIG. 14 is a flowchart representative of example machine readable instructions and/or example operations 1400 that may be executed, instantiated, and/or performed by programmable circuitry to detect a pace pulse. The example machine-readable instructions and/or the example operations 1400 of FIG. 14 include the ECG electrodes 106 gathering ECG signals (block 1402). The filters 108 filter the ECG signal (block 1404).

Figure 15:
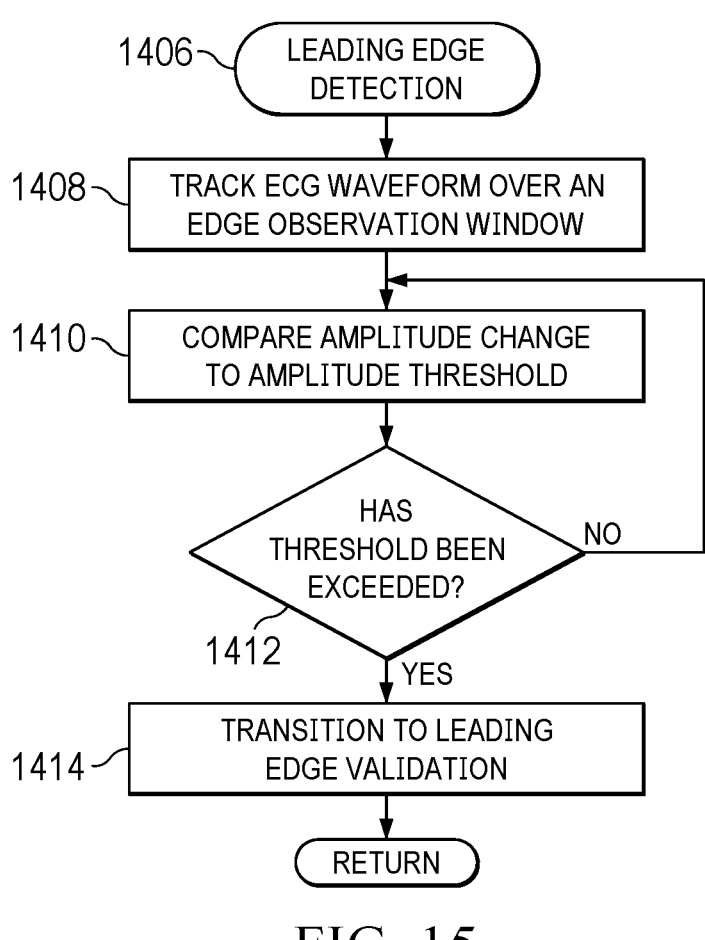

The leading edge detection circuitry 202 detects a leading edge of a pace pulse (block 1406). FIG. 15 is a flowchart representative of example machine readable instructions and/or example operations 1406 that may be executed, instantiated, and/or performed by programmable circuitry to detect a leading edge of a pace pulse. The example machine-readable instructions and/or the example operations 1406 of FIG. 15 include the leading edge detection circuitry 202 tracking an ECG signal or waveform over an edge observation window (block 1408). The leading edge detection circuitry 202 compares one or more amplitude changes in the ECG signal to an amplitude threshold (block 1410). The leading edge detection circuitry 202 determines if the amplitude threshold has been exceeded (block 1412). If and/or when the leading edge detection circuitry 202 determines that the amplitude threshold has not been exceeded (block 1412: NO), the leading edge detection process 1406 continues with the leading edge detection circuitry 202 comparing one or more amplitude changes in the ECG signal to the amplitude threshold (block 1410). If and/or when the leading edge detection circuitry 202 determines that the amplitude threshold has been exceeded (block 1412: YES), the pace pulse detection circuitry 112 transitions to lead edge validation (block 1414).

Figure 16:
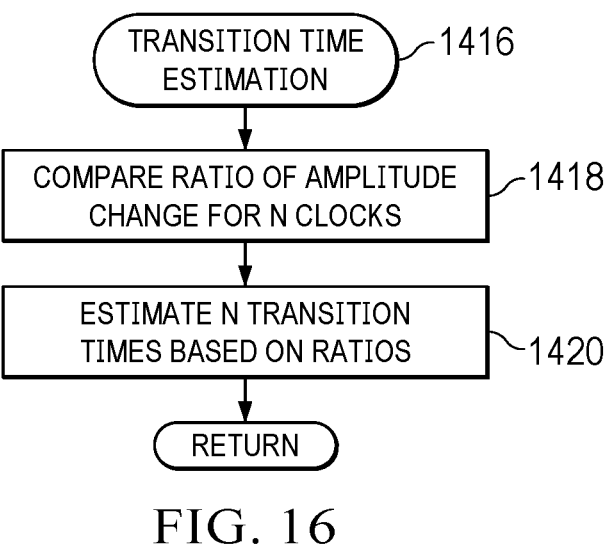

Returning to FIG. 14, the pace pulse detection operations 1400 include the transition time estimate circuitry 204 estimating the transition time (block 1416). FIG. 16 is a flowchart representative of example machine readable instructions and/or example operations 1416 that may be executed, instantiated, and/or performed by programmable circuitry to estimate a transition time of a leading edge of a pace pulse. The example machine-readable instructions and/or the example operations 1416 of FIG. 16 include the transition time estimate circuitry 204 comparing a ration of amplitude change for N number of clock cycles (blocks 1418). The transition time estimate circuitry 204 estimates N number of transition times based on the ratios (block 1420.

Returning to FIG. 14, the pace pulse detection operations 1400 include the leading edge validation circuitry 206 validating the leading edge of the pace pulse (block 1422). FIG. 17 is a flowchart representative of example machine readable instructions and/or example operations 1422 that may be executed, instantiated, and/or performed by programmable circuitry to validate a leading edge of a pace pulse. The example machine-readable instructions and/or the example operations 1422 of FIG. 17 include the leading edge validation circuitry 206 determining a metric based on amplitude changes and transition times (block 1424). For example, the leading edge validation circuitry 206 determines a FOM as disclosed herein. In some examples, the metric discussed with respect to FIG. 17 is the FOM disclosed above. The example leading edge validation process 1422 also includes the leading edge validation circuitry 206 comparing metrics to a metric threshold (block 1426). In some examples, the leading edge validation circuitry 206 determines if the metric threshold has been exceeded (block 1428). If and/or when the leading edge validation circuitry 206 determines that the metric threshold has not been exceeded (block 1428: NO), the leading edge validation circuitry 206 continues to compare metrics to a metric threshold (block 1426). If and/or when the leading edge validation circuitry 206 determines that the metric threshold has been exceeded (block 1428: YES), the leading edge validation circuitry 206 identifies a leading edge of a pace pulse (block 1430).

The leading edge validation circuitry 206 continues to compare metrics to the metric threshold as the ECG signal progresses (block 1432). The leading edge validation circuitry 206 determines if a metric falls below a scaled value of the metric threshold (block 1434). If and/or when the leading edge validation circuitry 206 determines that a metric does not fall below a scaled value of the metric threshold (block 1434: NO), the leading edge validation circuitry 206 continues to compare metrics to a metric threshold (block 1432). If and/or when the leading edge validation circuitry 206 determines that a metric does fall below a scaled value of the metric threshold (block 1434: YES), the leading edge validation circuitry 206 identifies an end of the leading edge of a pace pulse (block 1436), which, in some examples, is a validation of the leading edge.

Figure 18:
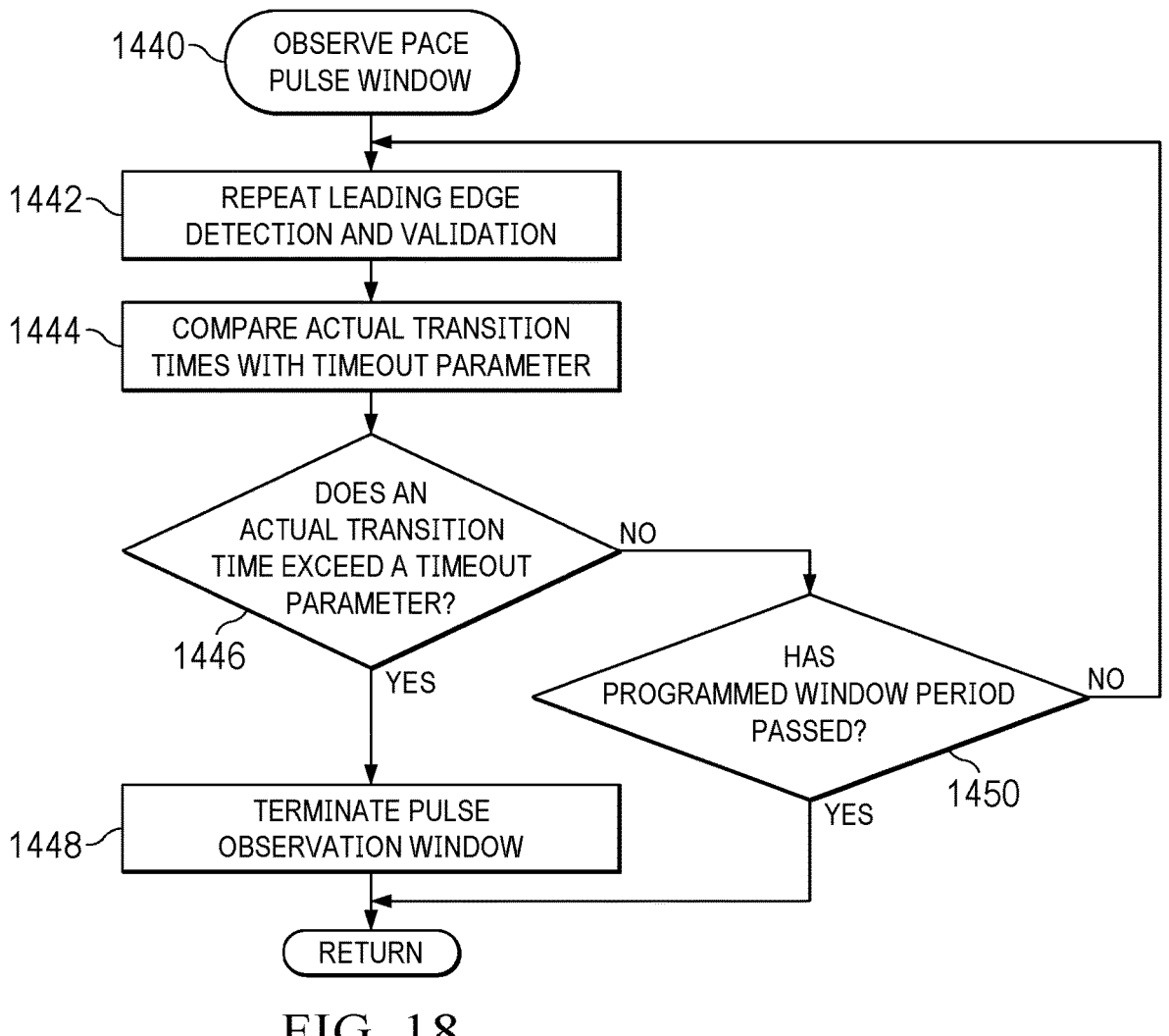

The leading edge validation circuitry 206 computes the actual transition time based on the detection of the leading edge and the identification of the end of the leading edge (block 1438). With the leading edge validated, the pace pulse observation circuitry 208 begins a pace or a pace pulse observation window (block 1440). FIG. 18 is a flowchart representative of example machine readable instructions and/or example operations 1440 that may be executed, instantiated, and/or performed by programmable circuitry to observe a pace pulse window. The example machine-readable instructions and/or the example operations 1440 of FIG. 18 include the leading edge detection circuitry 202, the transition time estimation circuitry 204, and the leading edge validation circuitry 206 repeating the leading edge detection and validation processes on the ECG signal during the pace pulse observation window (block 1442). Thus, in this example, block 1442 represents repetition of blocks 1406, 1416, and 1422.

During the pace pulse observation window, the pace pulse observation circuitry 208 compares actual transition times of the leading edge with a timeout parameter (block 1444). The pace pulse observation circuitry 208 determines if an actual transition time exceeds the timeout parameter (block 1446). If and/or when the pace pulse observation circuitry 208 determines that the actual transition time exceeds the timeout parameter (block 1446: YES), the pace pulse observation circuitry 208 terminates the pace pulse observation window (block 1448). In this example, the leading edge would have transitioned over too long a duration to be properly categorized or validated as a leading edge of a pace pulse. If and/or when the pace pulse observation circuitry 208 determines that the actual transition time has not exceeded the timeout parameter (block 1446: NO), the pace pulse observation circuitry 208 determines if a programmed window period has passed (block 1450).

A programmed window period may be based, for example, on a type and/or frequency of a pace pulse to be observed. For example, a programmed window period may be based on an expected pace pulse duration where a longer pace pulse duration would be detectable during a longer programmed window. If and/or when the pace pulse observation circuitry 208 determines that the programmed window period has not passed (block 1450: NO), the pace pulse window observation process 1440 continues with the leading edge detection circuitry 202, the transition time estimation circuitry 204, and the leading edge validation circuitry 206 repeating the leading edge detection and validation processes on the ECG signal during the pace pulse observation window (block 1442). If and/or when the pace pulse observation circuitry 208 determines that the programmed window period has passed (block 1450: YES), the pace pulse observation process 1440 closes.

Figure 19:
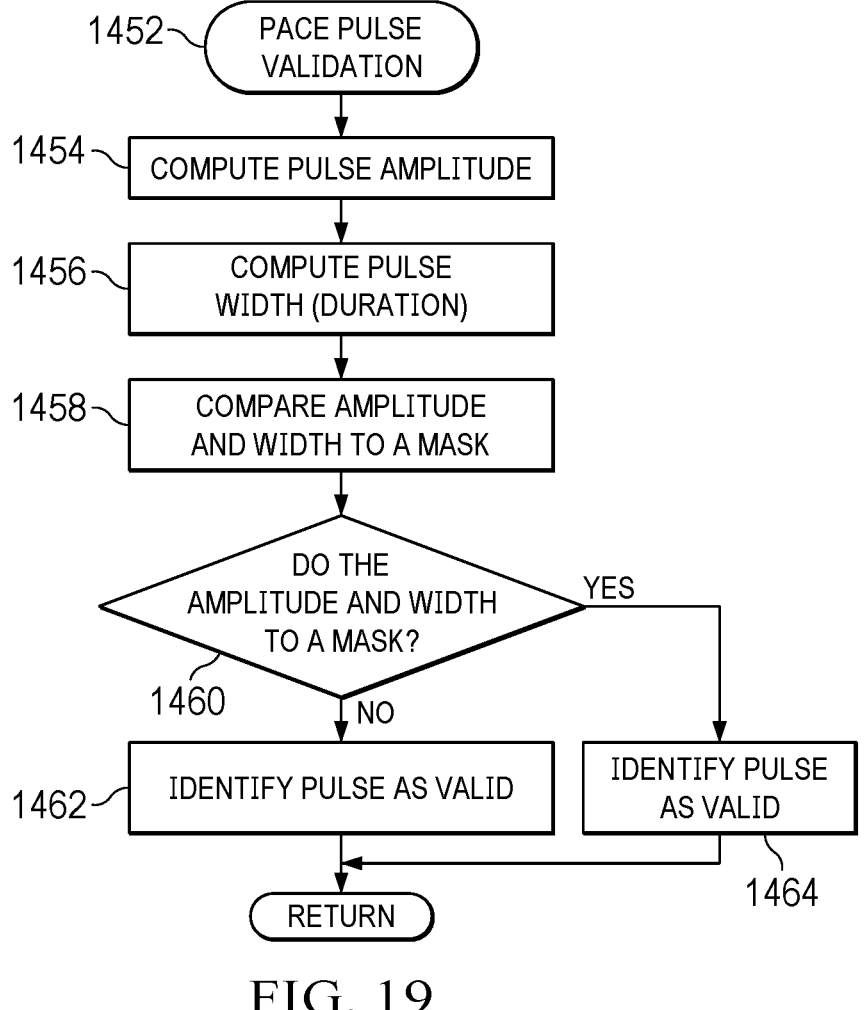

Returning to FIG. 14, the pace pulse detection process 1400 includes the pace pulse validation circuitry 210 validating the pace pulse (block 1452). FIG. 19 is a flowchart representative of example machine readable instructions and/or example operations 1452 that may be executed, instantiated, and/or performed by programmable circuitry to validate a pace pulse. The example machine-readable instructions and/or the example operations 1452 of FIG. 19 include the pace pulse validation circuitry 210 computing a pulse amplitude (block 1454). The pace pulse validation circuitry 210 also computes a pulse duration or width (block 1456). The pace pulse validation circuitry 210 compares the amplitude and width to a reference model or mask (block 1458).

The pace pulse validation circuitry 210 determines if the amplitude and width satisfy the mask (block 1460). For example, the pace pulse validation circuitry 210 determines if the values of the amplitude and the width meet reference values defined by the mask. If and/or when the pace pulse validation circuitry 210 determines that the amplitude and/or width do not satisfy the mask (block 1460: NO), the pace pulse validation circuitry 210 identifies the pace pulse as invalid (block 1462). If and/or when the pace pulse validation circuitry 210 determines that the amplitude and width do satisfy the mask (block 1460: YES), the pace pulse validation circuitry 210 identifies the pulse as valid (block 1464).

Returning to FIG. 14, the pace word composition circuitry 212 composes a pace word as disclosed herein (block 1466). The block window circuitry 214 observes a block window (block 1468). During a block window, the analysis of the ECG signal to identify and validate leading edges and pulses is paused. A duration of the block window may be based, for example, on a type and/or frequency of a pace pulse to be detected. For example, a biventricular pacemaker includes pace pulses that may be timed in a relatively quick succession. A relatively shorter block window could be used in this example scenario.

The example pace detection process 1400 also includes the ringing window circuitry 216 adjusting (e.g., by scaling) one or more of the thresholds used to compare an amplitude, identify a leading edge, compare a metric (e.g., a FOM). In some examples, one or more of these thresholds are scaled down to detect signals of smaller amplitudes that may be ringing artifacts and not pace pulses. With the scaled thresholds, the ringing window circuitry 216 observes a ringing window (block 1472).

The external transmission circuitry 220 externally transmits the data (block 1474). For example, the data may include the composed pace word and/or a combination of valid pace pulses. In some examples, the external transmission circuitry 220 transmits the data to a clinical ECG machine. Transmission of data related to valid pace pulses and not all of the raw ECG data saves power and processing requirements.

Figure 20:
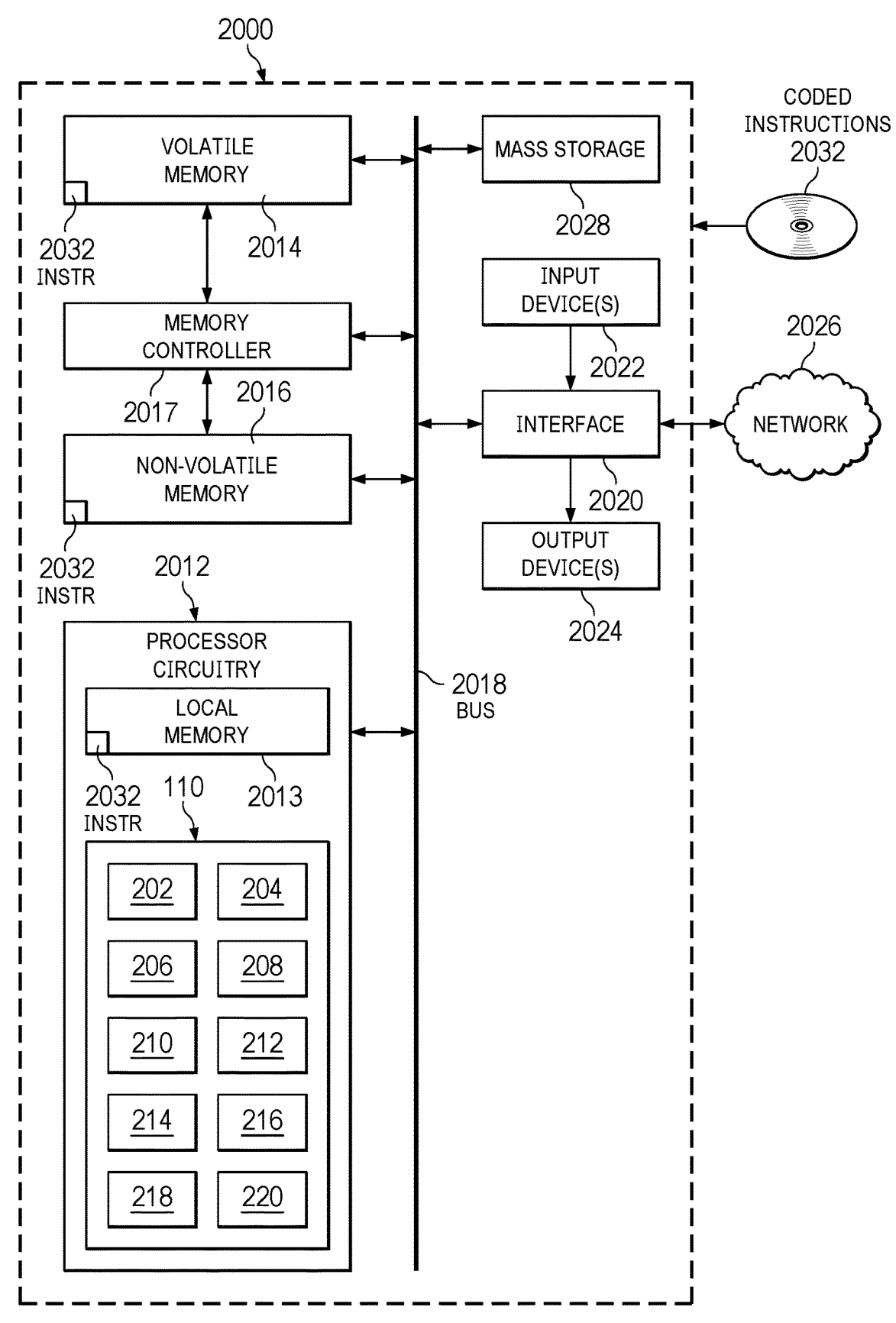
FIG. 20 is a block diagram of an example processing platform including programmable circuitry structured to execute, instantiate, and/or perform the example machine readable instructions and/or perform the example operations of FIGS. 12-19 to implement the pace pulse detection circuitry of FIG. 2.

FIG. 20 is a block diagram of an example programmable circuitry platform 2000 structured to execute and/or instantiate the example machine-readable instructions and/or the example operations of FIGS. 12-19 to implement the pace pulse detection circuitry 112 of FIG. 2. The programmable circuitry platform 2000 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, a headset (e.g., an augmented reality (AR) headset, a virtual reality (VR) headset, etc.) or other wearable device, or any other type of computing and/or electronic device.

The programmable circuitry platform 2000 of the illustrated example includes programmable circuitry 2012. The programmable circuitry 2012 of the illustrated example is hardware. For example, the programmable circuitry 2012 can be implemented by one or more integrated circuits, logic circuits, FPGAs, microprocessors, CPUs, GPUs, DSPs, and/or microcontrollers from any desired family or manufacturer. The programmable circuitry 2012 may be implemented by one or more semiconductor based (e.g., silicon based) devices. In this example, the programmable circuitry 2012 implements the pace pulse detection circuitry 112, the leading edge detection circuitry 202, the transition time estimation circuitry 204, the leading edge validation circuitry 206, the pace pulse observation circuitry 208, the pace pulse validation circuitry 210, the pace word composition circuitry 212, the block window circuitry 214, the ringing window circuitry 216, the valid pace pulse combination circuitry 218, and the external transmission circuitry 220.

The programmable circuitry 2012 of the illustrated example includes a local memory 2013 (e.g., a cache, registers, etc.). The programmable circuitry 2012 of the illustrated example is in communication with main memory 2014, 2016, which includes a volatile memory 2014 and a non-volatile memory 2016, by a bus 2018. The volatile memory 2014 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 2016 may be implemented by flash memory and/or any other desired type of memory device. Access to the main memory 2014, 2016 of the illustrated example is controlled by a memory controller 2017. In some examples, the memory controller 2017 may be implemented by one or more integrated circuits, logic circuits, microcontrollers from any desired family or manufacturer, or any other type of circuitry to manage the flow of data going to and from the main memory 2014, 2016.

The programmable circuitry platform 2000 of the illustrated example also includes interface circuitry 2020. The interface circuitry 2020 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface. In some examples, the interface circuitry 2020 implements the external transmission circuitry 220.

In the illustrated example, one or more input devices 2022 are connected to the interface circuitry 2020. The input device(s) 2022 permit(s) a user (e.g., a human user, a machine user, etc.) to enter data and/or commands into the programmable circuitry 2012. The input device(s) 2022 can be implemented by, for example, an audio sensor, a microphone, a camera (still or video), a keyboard, a button, a mouse, a touchscreen, a trackpad, a trackball, an isopoint device, and/or a voice recognition system.

One or more output devices 2024 are also connected to the interface circuitry 2020 of the illustrated example. The output device(s) 2024 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 2020 of the illustrated example, thus, typically includes a graphics driver card, a graphics driver chip, and/or graphics processor circuitry such as a GPU.

The interface circuitry 2020 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 2026. The communication can be by, for example, an Ethernet connection, a digital subscriber line (DSL) connection, a telephone line connection, a coaxial cable system, a satellite system, a beyond-line-of-sight wireless system, a line-of-sight wireless system, a cellular telephone system, an optical connection, etc.

The programmable circuitry platform 2000 of the illustrated example also includes one or more mass storage discs or devices 2028 to store firmware, software, and/or data. Examples of such mass storage discs or devices 2028 include magnetic storage devices (e.g., floppy disk, drives, HDDs, etc.), optical storage devices (e.g., Blu-ray disks, CDs, DVDs, etc.), RAID systems, and/or solid-state storage discs or devices such as flash memory devices and/or SSDs.

The machine readable instructions 2032, which may be implemented by the machine readable instructions of FIGS. 12-19, may be stored in the mass storage device 2028, in the volatile memory 2014, in the non-volatile memory 2016, and/or on at least one non-transitory computer readable storage medium such as a CD or DVD which may be removable.

Figure 21:
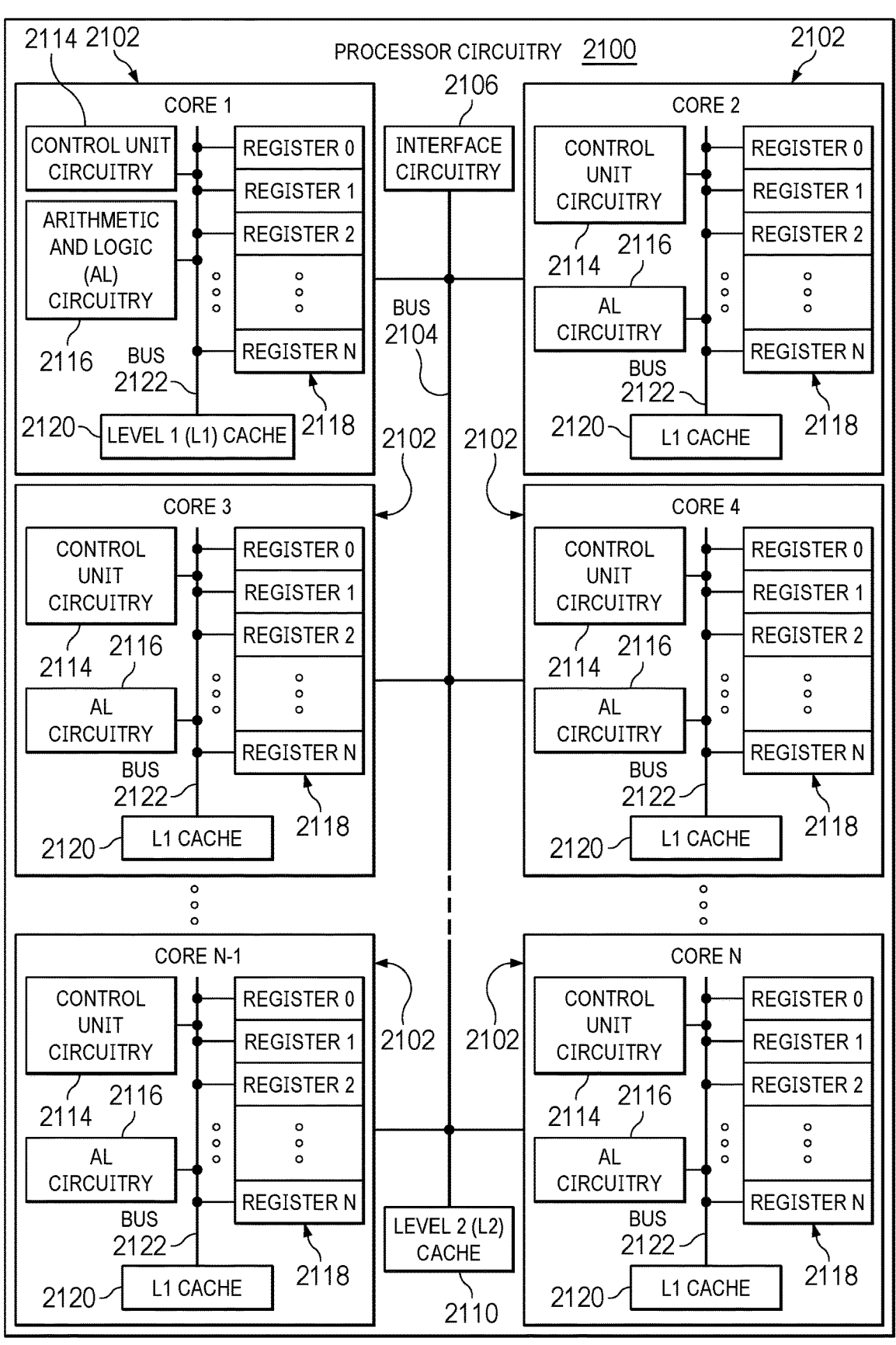
FIG. 21 is a block diagram of an example implementation of the programmable circuitry of FIG. 20.

FIG. 21 is a block diagram of an example implementation of the programmable circuitry 2012 of FIG. 20. In this example, the programmable circuitry 2012 of FIG. 20 is implemented by a microprocessor 2100. For example, the microprocessor 2100 may be a general-purpose microprocessor (e.g., general-purpose microprocessor circuitry). The microprocessor 2100 executes some or all of the machine-readable instructions of the flowcharts of FIGS. 12-19 to effectively instantiate the circuitry of FIG. 2 as logic circuits to perform operations corresponding to those machine readable instructions. In some such examples, the circuitry of FIG. pace pulse detection circuitry 112 is instantiated by the hardware circuits of the microprocessor 2100 in combination with the machine-readable instructions. For example, the microprocessor 2100 may be implemented by multi-core hardware circuitry such as a CPU, a DSP, a GPU, an XPU, etc. Although it may include any number of example cores 2102 (e.g., 1 core), the microprocessor 2100 of this example is a multi-core semiconductor device including N cores. The cores 2102 of the microprocessor 2100 may operate independently or may cooperate to execute machine readable instructions. For example, machine code corresponding to a firmware program, an embedded software program, or a software program may be executed by one of the cores 2102 or may be executed by multiple ones of the cores 2102 at the same or different times. In some examples, the machine code corresponding to the firmware program, the embedded software program, or the software program is split into threads and executed in parallel by two or more of the cores 2102. The software program may correspond to a portion or all of the machine readable instructions and/or operations represented by the flowcharts of FIGS. 12-19.

The cores 2102 may communicate by a first example bus 2104. In some examples, the first bus 2104 may be implemented by a communication bus to effectuate communication associated with one(s) of the cores 2102. For example, the first bus 2104 may be implemented by at least one of an Inter-Integrated Circuit (I2C) bus, a Serial Peripheral Interface (SPI) bus, a PCI bus, or a PCIe bus. Additionally or alternatively, the first bus 2104 may be implemented by any other type of computing or electrical bus. The cores 2102 may obtain data, instructions, and/or signals from one or more external devices by example interface circuitry 2106. The cores 2102 may output data, instructions, and/or signals to the one or more external devices by the interface circuitry 2106. Although the cores 2102 of this example include example local memory 2120 (e.g., Level 1 (L1) cache that may be split into an L1 data cache and an L1 instruction cache), the microprocessor 2100 also includes example shared memory 2110 that may be shared by the cores (e.g., Level 2 (L2 cache)) for high-speed access to data and/or instructions. Data and/or instructions may be transferred (e.g., shared) by writing to and/or reading from the shared memory 2110. The local memory 2120 of each of the cores 2102 and the shared memory 2110 may be part of a hierarchy of storage devices including multiple levels of cache memory and the main memory (e.g., the main memory 2014, 2016 of FIG. 20). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 2102 may be referred to as a CPU, DSP, GPU, etc., or any other type of hardware circuitry. Each core 2102 includes control unit circuitry 2114, arithmetic and logic (AL) circuitry (sometimes referred to as an ALU) 2116, a plurality of registers 2118, the local memory 2120, and a second example bus 2122. Other structures may be present. For example, each core 2102 may include vector unit circuitry, single instruction multiple data (SIMD) unit circuitry, load/store unit (LSU) circuitry, branch/jump unit circuitry, floating-point unit (FPU) circuitry, etc. The control unit circuitry 2114 includes semiconductor-based circuits structured to control (e.g., coordinate) data movement within the corresponding core 2102. The AL circuitry 2116 includes semiconductor-based circuits structured to perform one or more mathematic and/or logic operations on the data within the corresponding core 2102. The AL circuitry 2116 of some examples performs integer based operations. In other examples, the AL circuitry 2116 also performs floating-point operations. In yet other examples, the AL circuitry 2116 may include first AL circuitry that performs integer-based operations and second AL circuitry that performs floating-point operations. In some examples, the AL circuitry 2116 may be referred to as an Arithmetic Logic Unit (ALU).

The registers 2118 are semiconductor-based structures to store data and/or instructions such as results of one or more of the operations performed by the AL circuitry 2116 of the corresponding core 2102. For example, the registers 2118 may include vector register(s), SIMD register(s), general-purpose register(s), flag register(s), segment register(s), machine-specific register(s), instruction pointer register(s), control register(s), debug register(s), memory management register(s), machine check register(s), etc. The registers 2118 may be arranged in a bank as shown in FIG. 21. Alternatively, the registers 2118 may be organized in any other arrangement, format, or structure, such as by being distributed throughout the core 2102 to shorten access time. The second bus 2122 may be implemented by at least one of an I2C bus, a SPI bus, a PCI bus, or a PCIe bus.

Each core 2102 and/or, more generally, the microprocessor 2100 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 2100 is a semiconductor device fabricated to include many transistors interconnected to implement the structures described above in one or more integrated circuits (ICs) contained in one or more packages.

The microprocessor 2100 may include and/or cooperate with one or more accelerators (e.g., acceleration circuitry, hardware accelerators, etc.). In some examples, accelerators are implemented by logic circuitry to perform certain tasks more quickly and/or efficiently than can be done by a general-purpose processor. Examples of accelerators include ASICs and FPGAs such as those discussed herein. A GPU, DSP and/or other programmable device can also be an accelerator. Accelerators may be on-board the microprocessor 2100, in the same chip package as the microprocessor 2100 and/or in one or more separate packages from the microprocessor 2100.

Figure 22:
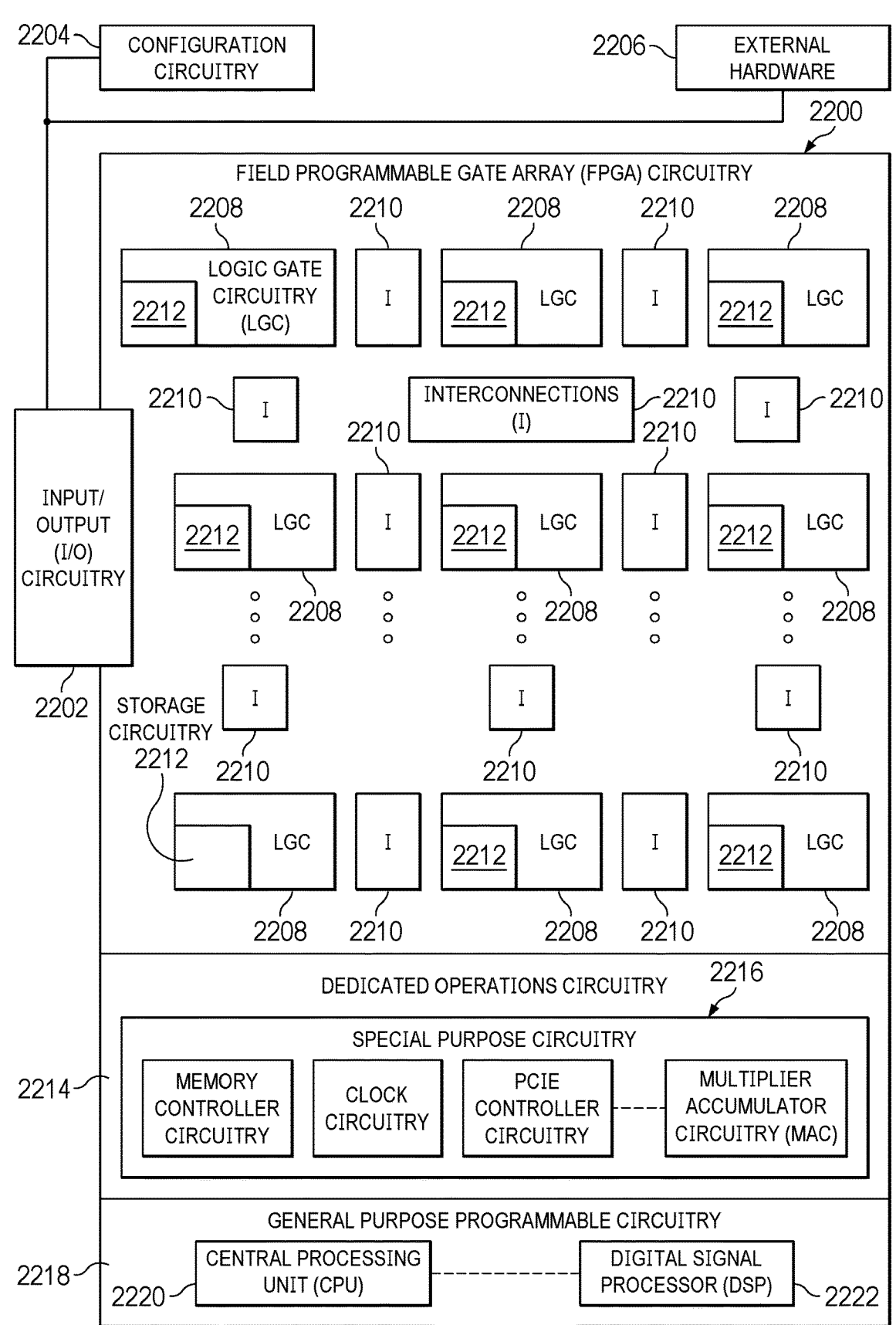
FIG. 22 is a block diagram of another example implementation of the programmable circuitry of FIG. 20.

FIG. 22 is a block diagram of another example implementation of the programmable circuitry 2012 of FIG. 20. In this example, the programmable circuitry 2012 is implemented by FPGA circuitry 2200. For example, the FPGA circuitry 2200 may be implemented by an FPGA. The FPGA circuitry 2200 can be used, for example, to perform operations that could otherwise be performed by the example microprocessor 2100 of FIG. 21 executing corresponding machine readable instructions. However, once configured, the FPGA circuitry 2200 instantiates the operations and/or functions corresponding to the machine readable instructions in hardware and, thus, can often execute the operations/functions faster than they could be performed by a general-purpose microprocessor executing the corresponding software.

More specifically, in contrast to the microprocessor 2100 of FIG. 21 described above (which is a general purpose device that may be programmed to execute some or all of the machine readable instructions represented by the flowchart(s) of FIGS. 12-19 but whose interconnections and logic circuitry are fixed once fabricated), the FPGA circuitry 2200 of the example of FIG. 22 includes interconnections and logic circuitry that may be configured, structured, programmed, and/or interconnected in different ways after fabrication to instantiate, for example, some or all of the operations/functions corresponding to the machine readable instructions represented by the flowchart(s) of FIGS. 12-19. In particular, the FPGA circuitry 2200 may be thought of as an array of logic gates, interconnections, and switches. The switches can be programmed to change how the logic gates are interconnected by the interconnections, effectively forming one or more dedicated logic circuits (unless and until the FPGA circuitry 2200 is reprogrammed). The configured logic circuits enable the logic gates to cooperate in different ways to perform different operations on data received by input circuitry. Those operations may correspond to some or all of the instructions (e.g., the software and/or firmware) represented by the flowchart(s) of FIGS. 12-19. As such, the FPGA circuitry 2200 may be configured and/or structured to effectively instantiate some or all of the operations/functions corresponding to the machine readable instructions of the flowchart(s) of FIGS. 12-19 as dedicated logic circuits to perform the operations/functions corresponding to those software instructions in a dedicated manner analogous to an ASIC. Therefore, the FPGA circuitry 2200 may perform the operations/functions corresponding to the some or all of the machine readable instructions of FIGS. 12-19 faster than the general-purpose microprocessor can execute the same.

In the example of FIG. 22, the FPGA circuitry 2200 is configured and/or structured in response to being programmed (and/or reprogrammed one or more times) based on a binary file. In some examples, the binary file may be compiled and/or generated based on instructions in a hardware description language (HDL) such as Lucid, Very High Speed Integrated Circuits (VHSIC) Hardware Description Language (VHDL), or Verilog. For example, a user (e.g., a human user, a machine user, etc.) may write code or a program corresponding to one or more operations/functions in an HDL; the code/program may be translated into a low-level language as needed; and the code/program (e.g., the code/program in the low-level language) may be converted (e.g., by a compiler, a software application, etc.) into the binary file. In some examples, the FPGA circuitry 2200 of FIG. 22 may access and/or load the binary file to cause the FPGA circuitry 2200 of FIG. 22 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 2200 of FIG. 22 to cause configuration and/or structuring of the FPGA circuitry 2200 of FIG. 22, or portion(s) thereof.

In some examples, the binary file is compiled, generated, transformed, and/or otherwise output from a uniform software platform utilized to program FPGAs. For example, the uniform software platform may translate first instructions (e.g., code or a program) that correspond to one or more operations/functions in a high-level language (e.g., C, C++, Python, etc.) into second instructions that correspond to the one or more operations/functions in an HDL. In some such examples, the binary file is compiled, generated, and/or otherwise output from the uniform software platform based on the second instructions. In some examples, the FPGA circuitry 2200 of FIG. 22 may access and/or load the binary file to cause the FPGA circuitry 2200 of FIG. 22 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 2200 of FIG. 22 to cause configuration and/or structuring of the FPGA circuitry 2200 of FIG. 22, or portion(s) thereof.

The FPGA circuitry 2200 of FIG. 22, includes example input/output (I/O) circuitry 2202 to obtain and/or output data to/from example configuration circuitry 2204 and/or external hardware 2206. For example, the configuration circuitry 2204 may be implemented by interface circuitry that may obtain a binary file, which may be implemented by a bit stream, data, and/or machine-readable instructions, to configure the FPGA circuitry 2200, or portion(s) thereof. In some such examples, the configuration circuitry 2204 may obtain the binary file from a user, a machine (e.g., hardware circuitry (e.g., programmable or dedicated circuitry) that may implement an Artificial Intelligence/Machine Learning (AI/ML) model to generate the binary file), etc., and/or any combination(s) thereof). In some examples, the external hardware 2206 may be implemented by external hardware circuitry. For example, the external hardware 2206 may be implemented by the microprocessor 2100 of FIG. 21.

The FPGA circuitry 2200 also includes an array of example logic gate circuitry 2208, a plurality of example configurable interconnections 2210, and example storage circuitry 2212. The logic gate circuitry 2208 and the configurable interconnections 2210 are configurable to instantiate one or more operations/functions that may correspond to at least some of the machine readable instructions of FIGS. 12-19 and/or other desired operations. The logic gate circuitry 2208 shown in FIG. 22 is fabricated in blocks or groups. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 2208 to enable configuration of the electrical structures and/or the logic gates to form circuits to perform desired operations/functions. The logic gate circuitry 2208 may include other electrical structures such as look-up tables (LUTs), registers (e.g., flip-flops or latches), multiplexers, etc.

The configurable interconnections 2210 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 2208 to program desired logic circuits.

The storage circuitry 2212 of the illustrated example is structured to store result(s) of the one or more of the operations performed by corresponding logic gates. The storage circuitry 2212 may be implemented by registers or the like. In the illustrated example, the storage circuitry 2212 is distributed amongst the logic gate circuitry 2208 to facilitate access and increase execution speed.

The example FPGA circuitry 2200 of FIG. 22 also includes example dedicated operations circuitry 2214. In this example, the dedicated operations circuitry 2214 includes special purpose circuitry 2216 that may be invoked to implement commonly used functions to avoid the need to program those functions in the field. Examples of such special purpose circuitry 2216 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 2200 may also include example general purpose programmable circuitry 2218 such as an example CPU 2220 and/or an example DSP 2222. Other general purpose programmable circuitry 2218 may additionally or alternatively be present such as a GPU, an XPU, etc., that can be programmed to perform other operations.

Although FIGS. 21 and 22 illustrate two example implementations of the programmable circuitry 2012 of FIG. 20, many other approaches are contemplated. For example, FPGA circuitry may include an on-board CPU, such as one or more of the example CPU 2220 of FIG. 21. Therefore, the programmable circuitry 2012 of FIG. 20 may additionally be implemented by combining at least the example microprocessor 2100 of FIG. 21 and the example FPGA circuitry 2200 of FIG. 22. In some such hybrid examples, one or more cores 2102 of FIG. 21 may execute a first portion of the machine readable instructions represented by the flowchart(s) of FIGS. 12-19 to perform first operation(s)/ function(s), the FPGA circuitry 2200 of FIG. 22 may be configured and/or structured to perform second operation(s)/function(s) corresponding to a second portion of the machine readable instructions represented by the flowcharts of FIG. 12-19, and/or an ASIC may be configured and/or structured to perform third operation(s)/function(s) corresponding to a third portion of the machine readable instructions represented by the flowcharts of FIGS. 12-19.

It should be understood that some or all of the circuitry of FIG. 2 may, thus, be instantiated at the same or different times. For example, same and/or different portion(s) of the microprocessor 2100 of FIG. 21 may be programmed to execute portion(s) of machine-readable instructions at the same and/or different times. In some examples, same and/or different portion(s) of the FPGA circuitry 2200 of FIG. 22 may be configured and/or structured to perform operations/functions corresponding to portion(s) of machine-readable instructions at the same and/or different times.

In some examples, some or all of the circuitry of FIG. 2 may be instantiated, for example, in one or more threads executing concurrently and/or in series. For example, the microprocessor 2100 of FIG. 21 may execute machine readable instructions in one or more threads executing concurrently and/or in series. In some examples, the FPGA circuitry 2200 of FIG. 22 may be configured and/or structured to carry out operations/functions concurrently and/or in series. Moreover, in some examples, some or all of the circuitry of FIG. 2 may be implemented within one or more virtual machines and/or containers executing on the microprocessor 2100 of FIG. 21.

In some examples, the programmable circuitry 2012 of FIG. 20 may be in one or more packages. For example, the microprocessor 2100 of FIG. 21 and/or the FPGA circuitry 2200 of FIG. 22 may be in one or more packages. In some examples, an XPU may be implemented by the programmable circuitry 2012 of FIG. 20, which may be in one or more packages. For example, the XPU may include a CPU (e.g., the microprocessor 2100 of FIG. 21, the CPU 2220 of FIG. 22, etc.) in one package, a DSP (e.g., the DSP 2222 of FIG. 22) in another package, a GPU in yet another package, and an FPGA (e.g., the FPGA circuitry 2200 of FIG. 22) in still yet another package.

From the foregoing, it will be appreciated that example systems, apparatus, articles of manufacture, and methods have been disclosed that detect valid pace pulses in ECG systems. Disclosed systems, apparatus, articles of manufacture, and methods improve the efficiency of using a computing device by identifying valid pace pulses in an AFE and transmitting data related to valid pace pulses to, for example, an ECG clinical machine. This saves processing and power consumption that would have been used to transmit the raw ECG data to the ECG clinical machine for analysis therein. In addition, the disclosed mode to gate external pace data transmission (for software detection) by an internal detection window greatly reduces the payload of pace data that is to be transferred between the AFE and the MCU, resulting in high power saving. Disclosed systems, apparatus, articles of manufacture, and methods are accordingly directed to one or more improvement(s) in the operation of a machine such as a computer or other electronic and/or mechanical device.

In addition, in some examples, the definition of a ringing window and the derivation of the amplitude and metric (e.g., FOM) thresholds in the ringing window are scaled versions of peak values from a previous pace observation window, which helps prevent spurious detection due to ringing from filter artefacts. The examples disclosed herein also enable detection of a valid closely spaced second pulse as in the case of a biventricular pacer.

Examples disclosed herein also increase the range of pace widths and amplitudes that can be detected by decreasing noise in the signal chain and identifying transient artifacts from the filters (e.g., ringing). In addition, the examples disclosed herein enable a detection and readout of actual pace pulse or leading edge data, which is not possible with convention methods in which series of filters distort the pace waveform. The pace pulse detector 102 enables the development of scalable medical instrumentation systems at significantly reduced size, power, and overall cost. Also, several parameters associated with the examples disclosed herein are programmable, enabling robust detection of existing and futuristic pacemakers.

Unless specifically stated otherwise, descriptors such as "first," "second," "third," etc., are used herein without imputing or otherwise indicating any meaning of priority, physical order, arrangement in a list, and/or ordering in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly within the context of the discussion (e.g., within a claim) in which the elements might, for example, otherwise share a same name.

As used herein, "approximately" and "about" modify their subjects/values to recognize the potential presence of variations that occur in real world applications. For example, "approximately" and "about" may modify dimensions that may not be exact due to manufacturing tolerances and/or other real world imperfections as will be understood by persons of ordinary skill in the art. For example, "approximately" and "about" may indicate such dimensions may be within a tolerance range of +/−10% unless otherwise specified in the below description.

As used herein "substantially real time" refers to occurrence in a near instantaneous manner recognizing there may be real world delays for computing time, transmission, etc. Thus, unless otherwise specified, "substantially real time" refers to real time+/−1 second.

As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, "programmable circuitry" is defined to include (i) one or more special purpose electrical circuits (e.g., an application specific circuit (ASIC)) structured to perform specific operation(s) and including one or more semiconductor-based logic devices (e.g., electrical hardware implemented by one or more transistors), and/or (ii) one or more general purpose semiconductor-based electrical circuits programmable with instructions to perform specific functions(s) and/or operation(s) and including one or more semiconductor-based logic devices (e.g., electrical hardware implemented by one or more transistors). Examples of programmable circuitry include programmable microprocessors such as Central Processor Units (CPUs) that may execute first instructions to perform one or more operations and/or functions, Field Programmable Gate Arrays (FPGAs) that may be programmed with second instructions to cause configuration and/or structuring of the FPGAs to instantiate one or more operations and/or functions corresponding to the first instructions, Graphics Processor Units (GPUs) that may execute first instructions to perform one or more operations and/or functions, Digital Signal Processors (DSPs) that may execute first instructions to perform one or more operations and/or functions, XPUs, Network Processing Units (NPUs) one or more microcontrollers that may execute first instructions to perform one or more operations and/or functions and/or integrated circuits such as Application Specific Integrated Circuits (ASICs). For example, an XPU may be implemented by a heterogeneous computing system including multiple types of programmable circuitry (e.g., one or more FPGAs, one or more CPUs, one or more GPUs, one or more NPUs, one or more DSPs, etc., and/or any combination(s) thereof), and orchestration technology (e.g., application programming interface(s) (API(s)) that may assign computing task(s) to whichever one(s) of the multiple types of programmable circuitry is/are suited and available to perform the computing task(s).

As used herein "satisfying" a threshold is defined to indicate meeting a threshold or meeting or fulfilling one or more criteria. In some examples, a threshold is satisfied if exceeded. In some examples, a threshold is satisfied if not exceeded.

Example systems, apparatus, articles of manufacture, and methods are disclosed to detect a pace pulse in an ECG signal. Example 1 includes an apparatus that includes: memory configured to include computer readable instructions; and programmable circuitry configured to execute the instructions to: identify a leading edge of a pulse in an input signal responsive to on an amplitude change; identify a transition time of the leading edge of the pulse; validate the leading edge of the pulse based on the amplitude change and transition time; identify a trailing edge of the pulse; determine a width of the pulse between the leading edge and the trailing edge; and validate the pulse based on the width.

Example 2 includes the apparatus of Example 1, wherein to validate the leading edge of the pulse, the programmable circuitry is configured to: determine a metric (e.g., a FOM) based on the amplitude change and the transition time; compare the metric to a metric threshold; and validate the leading edge of the pulse when the metric satisfies the metric threshold.

Example 3 includes the apparatus of either Examples 1 or 2, wherein the programmable circuitry is configured to identify N number of amplitude changes and N number of transition times for a respective N number of clock cycles in the input signal, and to validate the leading edge of the pulse, the programmable circuitry is configured to: determine N number of metrics based on the respective amplitude change and the respective transition time; compare respective ones of the metrics to respective metric thresholds; and validate the leading edge of the pulse when a first metric of the metrics satisfies a respective first metric threshold and a second metric for a subsequent clock cycle is less than the first metric.

Example 4 includes the apparatus of Example 3, wherein the programmable circuitry is configured to identify an end of the leading edge of the pulse based on a comparison of the first metric threshold and a second metric threshold for the second metric.

Example 5 includes the apparatus of either Examples 3 or 4, wherein the programmable circuitry is configured to identify an end of the leading edge of the pulse when a second metric threshold for the second metric is less than a scaled value of the first metric threshold.

Example 6 include the apparatus of any of Examples 3-5, wherein the programmable circuitry is configured to identify the trailing edge of the pulse.

Example 7 includes the apparatus of any of Examples 1-6, wherein the programmable circuitry is configured to observe a block window after a validation of the pulse, during the block window the programmable circuitry suspends identifying leading edges.

Example 8 includes the apparatus of any of Examples 1-7, wherein the programmable circuitry is configured to observe a ringing window after a validation of the pulse, during the ringing window the metric thresholds are scaled down.

Example 9 includes the apparatus of Example 8, wherein the ringing window includes a first ringing sub-window and a second ringing sub-window subsequent to the first ringing sub-window, the metric thresholds scaled down by a first factor in the first ringing sub-window, and the metric thresholds scaled down by a second factor in the second ringing sub-window, the second factor greater than the first factor.

Example 10 includes a method comprising: identifying a leading edge of a pulse in a cardiac signal responsive to an amplitude change; identifying a trailing edge of the pulse; determining a width of the pulse between the leading edge and the trailing edge; validating the pulse based on the width; and observing a ringing window after a validation of the pulse, during the ringing window a threshold for identifying the leading edge is scaled.

Example 11 includes the method of Example 10, further including: identifying an amplitude change in the cardiac signal during the ringing window; and categorizing the amplitude change as a ringing artifact based on the scaled threshold.

Example 12 includes the method of either of Examples 10 or 11, wherein the ringing window includes a first ringing sub-window and a second ringing sub-window subsequent to the first ringing sub-window, the threshold is scaled by a first factor in the first ringing sub-window, and by a second factor in the second ringing sub-window, the second factor greater than the first factor.

Example 13 includes the method of any of Examples 10-12, wherein the threshold is scaled down.

Example 14 includes the method of any of Examples 10-13, further including: observing a block window after validating the pulse; and suspending the identifying of leading edges during the block window.

Example 15 includes the method of Example 14 further including observing the block window before observing the ringing window.

Example 16 includes the method of any of Examples 10-15, wherein the threshold is scaled based on a peak amplitude change in the cardiac signal.

Example 17 includes anon-transitory machine readable storage medium that includes instructions to cause programmable circuitry to: identify a leading edge of a pulse in an input signal responsive to an amplitude change; identify a transition time of the leading edge of the pulse; validate the leading edge of the pulse based on the amplitude change and transition time; identify a trailing edge of the pulse; determine a width of the pulse between the leading edge and the trailing edge; validate the pulse based on the width; and observe a ringing window after validating the pulse, during the ringing window a threshold for identifying the leading edge is scaled.

Example 18 includes the storage medium of Example 17, wherein the threshold for identifying the leading edge is a metric threshold based on the amplitude change and the transition time, and the instructions cause the programmable circuitry to: identify N number of amplitude changes and N number of transition times for a respective N number of clock cycles in the ECG signals; and validate the leading edge of the pulse by: determining N number of metrics based on the respective amplitude change and the respective transition time; comparing respective ones of the metrics to respective metric thresholds; and validating the leading edge of the pulse when a first metric of the metrics satisfies a respective first metric threshold and a second metric for a subsequent clock cycle is less than the first metric.

Example 19 includes the storage medium of either of Examples 17 or 18, wherein the ringing window includes a plurality of sub-windows, and the instructions cause the programmable circuitry to scale the threshold for identifying the leading edge differently among the sub-windows.

Example 20 includes the storage medium of any of Examples 17-19, wherein the ringing window includes a plurality of sub-windows, and the instructions cause the programmable circuitry to increasingly scale the threshold for identifying the leading edge as the plurality of sub-windows progress in time.

The following claims are hereby incorporated into this Detailed Description by this reference. Although certain example systems, apparatus, articles of manufacture, and methods have been disclosed herein, the scope of coverage of this patent is not limited thereto. On the contrary, this patent covers all systems, apparatus, articles of manufacture, and methods fairly falling within the scope of the claims of this patent.

Modifications are possible in the described example, and other examples are possible, within the scope of the claims.

What is claimed is:

1. An apparatus comprising:
an electrocardiogram (ECG) circuit having an input and an output, the input of the ECG circuit adapted for attachment to a user, the ECG circuit configured to receive an ECG signal on the input of the ECG circuit, and transmit data related to validated pulses on the output of the ECG circuit;
memory configured to include computer readable instructions; and
programmable circuitry configured to execute the computer readable instructions to:
identify a leading edge of a pulse in the ECG signal responsive to an amplitude change in the ECG signal;
identify a transition time of the leading edge of the pulse;
validate the leading edge of the pulse based on the amplitude change and the transition time;
identify a trailing edge of the pulse;
determine a width of the pulse between the leading edge and the trailing edge;
validate the pulse based on the width of the pulse;
transmit data related to the pulse after the pulse has been validated; and
suspend identification of leading edges of subsequent pulses in the ECG signal during a time window after validating the pulse.

2. The apparatus of claim 1, wherein to validate the leading edge of the pulse, the programmable circuitry is configured to:

determine a metric based on the amplitude change and the transition time;
compare the metric to a metric threshold; and
validate the leading edge of the pulse when the metric satisfies the metric threshold.

3. The apparatus of claim 2, wherein the programmable circuitry is configured to observe a ringing window after a validation of the pulse, during the ringing window the metric threshold is scaled down.

4. The apparatus of claim 3, wherein the ringing window includes a first ringing sub-window and a second ringing sub-window subsequent to the first ringing sub-window, and wherein the metric threshold is scaled down by a first factor in the first ringing sub-window and scaled down by a second factor in the second ringing sub-window, the second factor greater than the first factor.

5. The apparatus of claim 1, wherein the programmable circuitry is configured to identify N number of amplitude changes and N number of transition times for a respective N number of clock cycles in the ECG signals, and to validate the leading edge of the pulse, the programmable circuitry is configured to:
determine N number of metrics based on a respective amplitude change and a respective transition time;
compare respective ones of the metrics to respective metric thresholds; and
validate the leading edge of the pulse when a first metric of the metrics satisfies a respective first metric threshold and a second metric for a subsequent clock cycle is less than the first metric.

6. The apparatus of claim 5, wherein the programmable circuitry is configured to identify an end of the leading edge of the pulse based on a comparison of the first metric threshold and a second metric threshold for the second metric.

7. The apparatus of claim 5, wherein the programmable circuitry is configured to identify an end of the leading edge of the pulse when a second metric threshold for the second metric is less than a scaled value of the first metric threshold.

8. The apparatus of claim 5, wherein the programmable circuitry is configured to identify the trailing edge of the pulse.

9. The apparatus of claim 1,
wherein a duration of the time window is programmable.

10. A method comprising:
receiving a cardiac signal on an input of electrocardiogram (ECG) analog front end (AFE) circuitry;
identifying a leading edge of a first pulse in the cardiac signal by comparing an amplitude change in the first pulse and a first threshold;
identifying a trailing edge of the first pulse;
determining a width of the first pulse between the leading edge and the trailing edge;
validating the first pulse based on the width;
transmitting data related to the validating of the first pulse on an output of the ECG AFE circuitry; and
identifying a leading edge of a second pulse in the cardiac signal by comparing an amplitude change for the second pulse to a second threshold during a ringing window after the validation of the first pulse, wherein the second threshold leading edge is scaled relative to the first threshold.

11. The method of claim 10, further comprising:
categorizing the amplitude change for the second pulse as a ringing artifact based on the second threshold.

12. The method of claim 10, wherein the ringing window includes a first ringing sub-window and a second ringing sub-window subsequent to the first ringing sub-window, wherein the method comprises using the second threshold during the first ringing sub-window and a third threshold during the second ringing sub-window, the second threshold scaled relative to the first threshold by a first factor, and the third threshold scaled relative to the first threshold by a second factor, the second factor greater than the first factor.

13. The method of claim 10, wherein the second threshold is scaled down relative to the first threshold.

14. The method of claim 10, further comprising:

observing a block window after validating the first pulse; and suspending identification of leading edges during the block window.

15. The method of claim 14 further comprising observing the block window before observing the ringing window.

16. The method of claim 10, wherein the second threshold is scaled relative to the first threshold based on a peak amplitude change in the cardiac signal.

17. An apparatus comprising:

electrocardiogram (ECG) analog front end (AFE) circuitry having an input and an output;

memory configured to store computer readable instructions; and processing circuitry coupled to the memory and configured to execute the computer readable instructions to:

receive a cardiac signal on the input of the ECG AFE circuitry;

identify a leading edge of a first pulse in the cardiac signal based on an amplitude change of the first pulse and a first threshold;

identify a transition time of the leading edge of the first pulse;

validate the leading edge of the first pulse based on the amplitude change of the first pulse and the transition time;

identify a trailing edge of the first pulse;

determine a width of the first pulse between the leading edge and the trailing edge;

validate the first pulse based on the width;

transmit data related to the first pulse on the output of the ECG AFE after validating the first pulse; and identifying a leading edge of a second pulse in the cardiac signal based on an amplitude change of the second pulse and a second threshold during a ringing window after validating the first pulse, wherein the second threshold is scaled relative to the first threshold.

18. The apparatus of claim 17, wherein the first threshold for identifying the leading edge of the first pulse is a metric threshold based on the amplitude change of the first pulse and the transition time, and the processing circuitry is further configured execute the computer readable instructions to:

identify N number of amplitude changes and N number of transition times for a respective N number of clock cycles in the cardiac signal; and validate the leading edge of the first pulse by:

determining N number of metrics based on respective amplitude changes and transition times of the N number of amplitude changes and N number of transition times;

comparing each of the metrics in the N number of metrics to a respective metric threshold; and validating the leading edge of the pulse when a first metric of the metrics satisfies a respective first metric threshold and a second metric for a subsequent clock cycle is less than the first metric.

19. The apparatus of claim 17, wherein the ringing window includes a plurality of sub-windows, and the processing circuitry is further configured to execute the instructions to scale the first threshold for identifying the leading edge differently among the sub-windows.

20. The apparatus of claim 17, wherein the ringing window includes a plurality of sub-windows, and the processing circuitry is further configured to execute the instructions to increasingly scale the first threshold for identifying the leading edge as the plurality of sub-windows progress in time.

\* \* \* \* \*